United States Patent
Guzi et al.

[11] Patent Number: 6,159,984
[45] Date of Patent: Dec. 12, 2000

[54] FARNESYL PROTEIN TRANSFERASE INHIBITORS

[75] Inventors: Timothy J. Guzi, Chatham; Dinanath F. Rane, Morganville, both of N.J.

[73] Assignee: Schering Corporation, Kenilworth, N.J.

[21] Appl. No.: 09/094,707

[22] Filed: Jun. 15, 1998

Related U.S. Application Data

[60] Provisional application No. 60/049,857, Jun. 17, 1997.

[51] Int. Cl.⁷ .................. A61K 31/4545; C07D 401/04; A61P 35/00
[52] U.S. Cl. .................. 514/290; 546/93; 514/232.8; 544/126
[58] Field of Search .............. 546/93; 514/290, 514/232.8; 544/126

[56] References Cited

U.S. PATENT DOCUMENTS

| | | | |
|---|---|---|---|
| 4,826,853 | 5/1989 | Piwinski et al. | 514/290 |
| 5,089,496 | 2/1992 | Piwinski et al. | 514/253 |
| 5,151,423 | 9/1992 | Piwinski et al. | 514/254 |
| 5,393,890 | 2/1995 | Syoji et al. | 546/80 |
| 5,661,152 | 8/1997 | Bishop et al. | 514/254 |
| 5,672,611 | 9/1997 | Doll et al. | 514/325 |
| 5,684,013 | 11/1997 | Afonso et al. | 514/290 |
| 5,696,121 | 12/1997 | Bishop et al. | 514/254 |
| 5,700,806 | 12/1997 | Doll et al. | 514/290 |
| 5,703,090 | 12/1997 | Afonso et al. | 514/290 |
| 5,712,280 | 1/1998 | Doll et al. | 514/253 |
| 5,714,609 | 2/1998 | Bishop et al. | 546/93 |
| 5,719,148 | 2/1998 | Bishop et al. | 514/228.2 |
| 5,721,236 | 2/1998 | Bishop et al. | 514/255 |
| 5,728,703 | 3/1998 | Bishop et al. | 514/254 |
| 5,807,853 | 9/1998 | Bishop | 514/228.2 |

FOREIGN PATENT DOCUMENTS

| | | |
|---|---|---|
| 0 270 818 | 6/1988 | European Pat. Off. |
| 0 396 083 | 11/1990 | European Pat. Off. |
| 0495484 | 7/1992 | European Pat. Off. |
| WO95/10515 | 4/1995 | WIPO |
| WO95/10516 | 4/1995 | WIPO |
| WO95/15949 | 6/1995 | WIPO |
| WO96/30018 | 10/1996 | WIPO |
| WO96/30362 | 10/1996 | WIPO |
| WO96/30363 | 10/1996 | WIPO |
| WO96/31477 | 10/1996 | WIPO |
| WO96/31478 | 10/1996 | WIPO |
| WO97/23478 | 7/1997 | WIPO |

OTHER PUBLICATIONS

Bishop et al., The Journal of Biological Chemistry, vol. 270, No. 15, pp. 30611–30618 (1995).
Njoroge et al., Bioorganic & Medicinal Chemistry Letters, vol. 6, No.24, pp. 2977–2982 (1996).
Njoroge FG et al. Biooganic & Medicinal Chemistry, 5, 101–113, 1997.
Khosravi–Far R et al. Cell Growth & Differentiation, 3, 461–9, Jul. 1992.

*Primary Examiner*—Evelyn Mei Huang
*Attorney, Agent, or Firm*—Henry C. Jeanette; Thomas D. Hoffman

[57] ABSTRACT

Novel compounds of the formula:

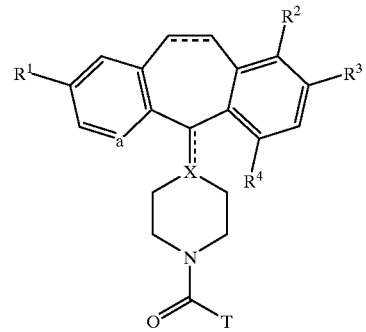

(1.0)

wherein a represents N or NO, $R^1$ and $R^3$ are halo, $R^2$ and $R^4$ are independently H or halo provided that at least one is H, X is C, CH or N, and T represents

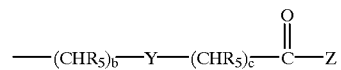

wherein $R_5$ is H $(C_1-C_6)$alkyl or a bond; b and c are independently 0 to 3 and Y is a three, four, five or six membered cycloalkyl ring, pyridyl, pyrazinyl or phenyl are disclosed. Pharmaceutical Compositions containing such compounds, methods of inhibiting farnesyl protein transferase and methods for treating tumor cells using such compounds or compositions are also disclosed.

24 Claims, No Drawings

FARNESYL PROTEIN TRANSFERASE INHIBITORS

This application claims the benefit of provisional application Ser. No. 60/049,857, filed on Jun. 17, 1997.

BACKGROUND

WO 95/10516, published Apr. 20, 1995 discloses tricyclic compounds useful for inhibiting farnesyl protein transferase.

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides compounds useful for the inhibition of farnesyl protein transferase (FPT). The compounds of this invention are represented by the formula:

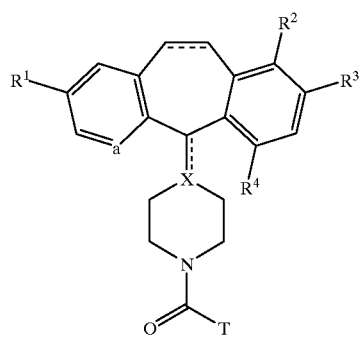

(1.0)

or a pharmaceutically acceptable salt or solvate thereof, wherein:

a represents N or NO—;

$R^1$ and $R^3$ are the same or different halo atom;

$R^2$ and $R^4$ are selected from H and halo, provided that at least one of $R^2$ and $R^4$ is H;

the dotted line (---) represents an optional bond;

X is N, C when the optional bond is present, or CH when the optional bond is absent;

T represents

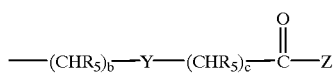

wherein $R_5$ represents H, $(C_1-C_6)$alkyl or a bond; b and c are independently 0 to 3 ; and Y represents

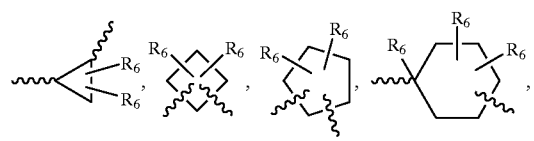

-continued

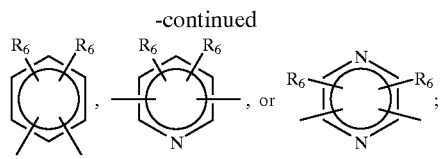

$R_6$ represents $(C_1-C_6)$alkyl or H;

Z represents $OR_7$, $R_7$ or $NR_8R_9$;

$R_7$ represents H, $(C_1-C_6)$alkyl or $(C_1-C_6)$alkyl substituted by $OR_5$, $COR_5$, phenyl or heteroaryl;

$R_8$ and $R_9$ independently represent H, OH, $(C_1-C_6)$alkyl or $(C_1-C_6)$ alkyl substituted by $OR_5$, —$COR_5$, phenyl, or heteroaryl, or $R_8$ and $R_9$ taken together with the nitrogen atom in $NR_8R_9$ form an unsubstituted or substituted five or six membered heterocyclic ring system containing carbon and one to four heteroatoms selected from N, O, S, SO or $SO_2$, said heterocyclic substituents being $(C_1-C_8)$ alkanoyl, $(C_1-C_6)$alkyl or $(C_1-C_6)$penthalo alkyl.

The invention also provides compounds represented by the formula:

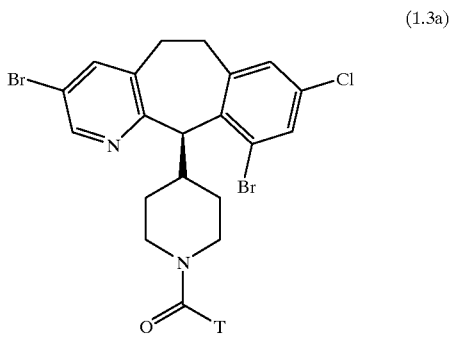

(1.3a)

wherein T is as defined above.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras.

Thus, this invention further provides a method of inhibiting farnesyl protein transferase, (e.g., ras farnesyl protein transferase) in mammals, especially humans, by the administration of an effective amount of the tricyclic compounds described above. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount of the tricyclic compounds, described herein, to a mammal (e.g., a human) in need of such treatment. In particular, this invention provides a method for inhibiting or treating the growth of tumors expressing an activated Ras oncogene by the administration of an effective amount of the above described compounds. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancer and prostate cancer.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The tricyclic compounds useful in the methods of this invention inhibit or treat the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity-against ras transformed cells.

DETAILED DESCRIPTION OF THE INVENTION

As used herein, the following terms are used as defined below unless otherwise indicated:

MH$^+$-represents the molecular ion plus hydrogen of the molecule in the mass spectrum;

Et (or ET)-represents ethyl ($C_2H_5$);

alkyl-represents straight and branched carbon chains and contains from one to twenty carbon atoms, preferably one to six carbon atoms;

halo-represents fluoro, chloro, bromo and iodo;

The following solvents and reagents are referred to herein by the abbreviations indicated: ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); 1-(3-dimethylaminopropyl)-3-ethyl carbodiimide hydrochloride (DEC); diisobutylaluminum hydride (DIBAL); and 4-methylmorpholine (NMM).

The positions in the tricyclic ring system are:

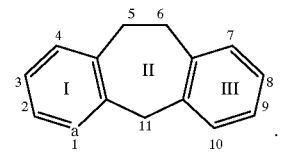

Preferred halo atoms for $R^1$, $R^2$, $R^3$, and $R^4$ in Formula 1.0 are selected from: Br, Cl or I, with Br and Cl being more preferred.

Compounds of Formula 1.0 include compounds of the formula:

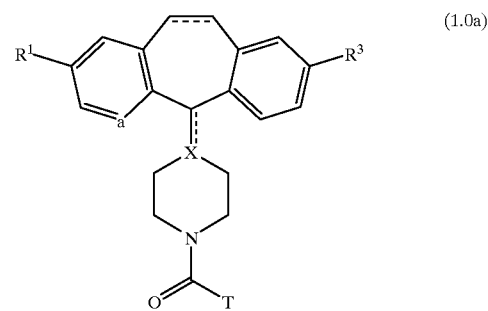

(1.0a)

wherein $R^1$ and $R^3$ are the same or different halo. Preferably, for these dihalo compounds, $R^1$ and $R^3$ are independently selected from Br or Cl, and more preferably $R^1$ is Br and $R^3$ is Cl. Preferably, X is CH or N, with CH being more preferred.

Compounds of Formula 1.0 include compounds of Formulas 1.1 and 1.2:

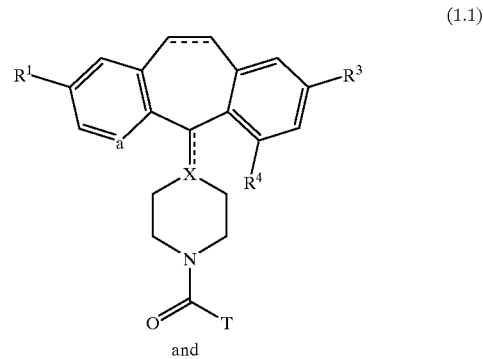

(1.1)

and

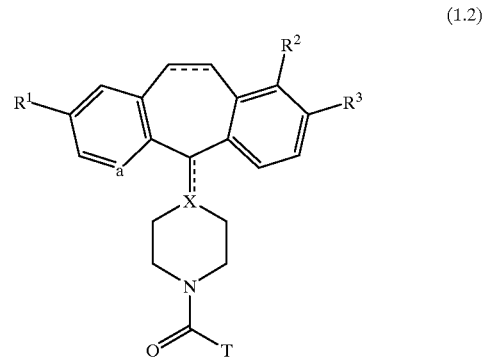

(1.2)

wherein $R^1$, $R^3$ and $R^4$ in Formula 1.1 are halo, and $R^1$, $R^2$ and $R^3$ in Formula 1.2 are halo. Compounds of Formula 1.1 are preferred.

Preferably, in Formula 1.1, $R^1$ is Br, $R^3$ is Cl, and $R^4$ is halo.

More preferably, in Formula 1.1, $R^1$ is Br, $R^3$ is Cl, and $R^4$ is Br.

Preferably, in Formula 1.2, $R^1$ is Br, $R^2$ is halo, and $R^3$ is Cl.

More preferably, in Formula 1.1, $R^1$ is Br, $R^2$ is Br, and $R^3$ is Cl.

Preferably, for compounds of Formulas 1.1 and 1.2, X is CH or N. For compounds of Formula 1.1, X is preferably CH.

Preferably, for the compounds of this invention, the optional bond between positions 5 and 6 (i.e., $C_5$–$C_6$) in the tricyclic system is absent.

Also, preferably, for the compounds of this invention, substituent a in Ring I represents N.

Those skilled in the art will appreciate that compounds of Formula 1.0 include compounds of Formulas 1.3 and 1.4:

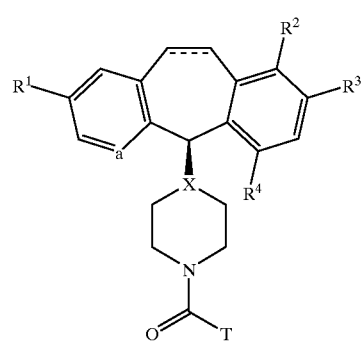

(1.3)

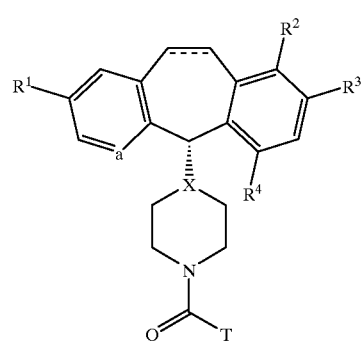

(1.4)

wherein X is CH or N, with compounds of 1.3 being preferred for compounds of Formula 1.1, and with compounds of Formula 1.4 being preferred for componds of Formula 1.2.

Thus, compounds of the invention include compounds of the formulas:

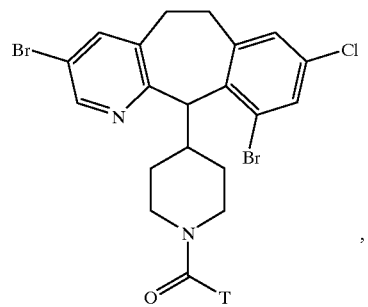

(1.5)

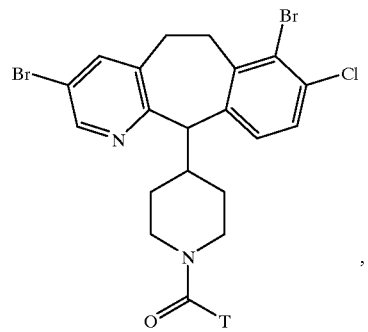

(1.6)

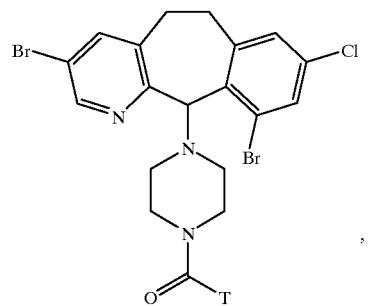

(1.7)

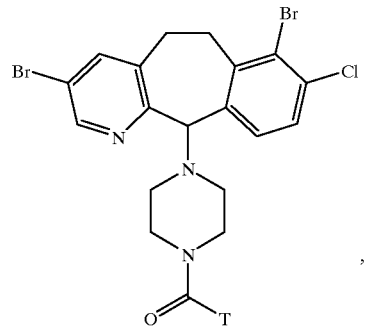

(1.8)

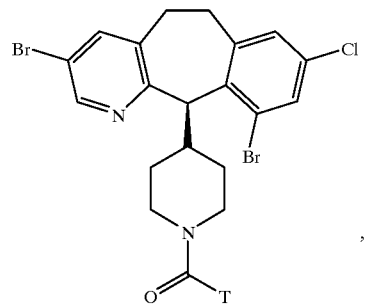

(1.9)

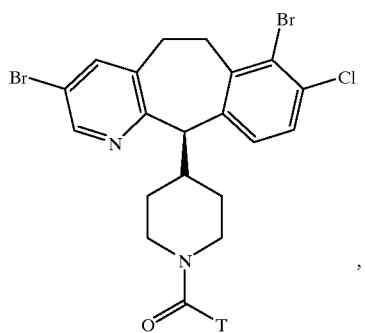 (1.10)

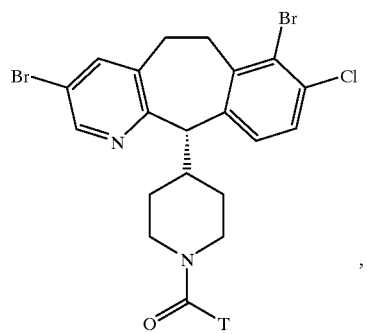 (1.14)

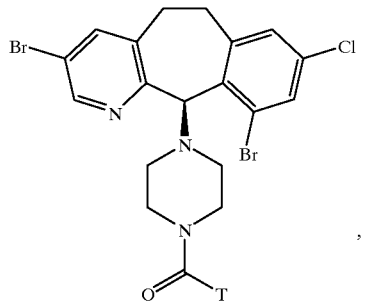 (1.11)

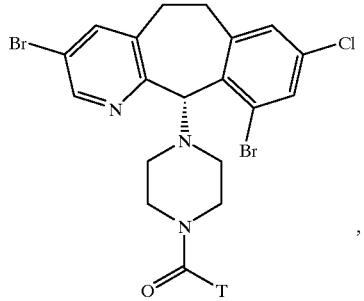 (1.15)

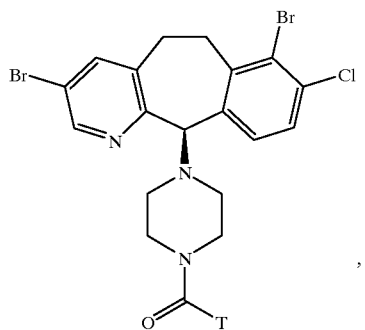 (1.12)

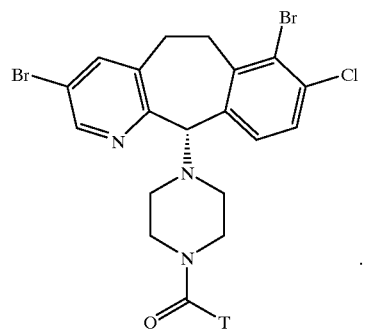 (1.16)

Compounds of Formula 1.9 are preferred.
T can represent

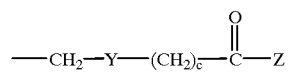

wherein c is 0 or 1, Y is cyclopropyl, cyclohexyl or phenyl and Z is OH, or $OR_5$, $NH_2$, $NR_8R_9$, $NHOR_5$ or $NH(C_1-C_6)$alkylCO$(C_1-C_6)$alkoxy wherein $R_5$, $R_8$ and $R_9$ each represent $(C_1-C_6)$alkyl.

Preferably substituent T is

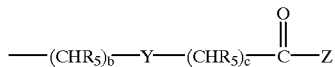

wherein $R_5$ represents H and b is 1; c is 0 or 1; Y is cyclohexyl or phenyl; and Z=OH or $OR_5$, $NH_2$, NHO$(C_1-C_6)$alkyl or $NH(C_1-C_6)$alkylCO$(C_1-C_6)$alkoxy.

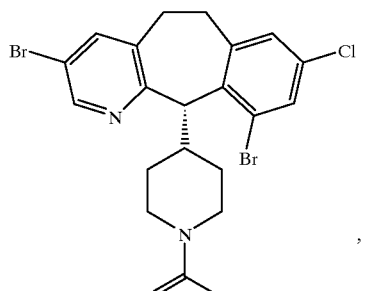 (1.13)

Most preferably, T represents:

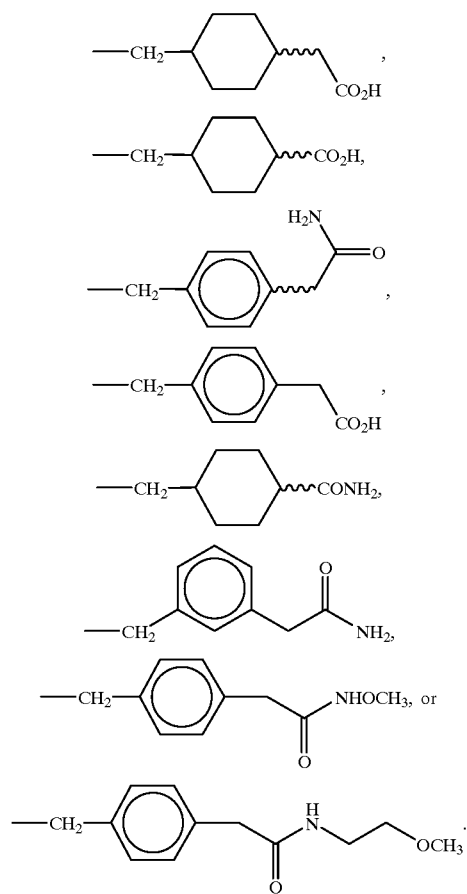

T may also be represented by the formula wherein $R_5$ represents H, and b=0, and c is 1, i.e.,

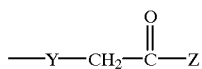

and Y is phenyl or cyclohexyl and Z is, for example, $NR_8R_9$ or $OR_7$ or b and c are each 0; and Y is phenyl or cyclopropyl and Z is $OR_7$ or $NR_8R_9$.

Typically T represents:

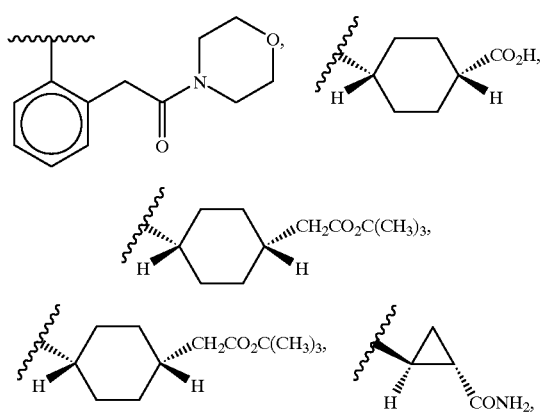

-continued

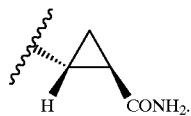

T may also be represented by the formula wherein $R_5$ represents a bond and b and c are each 1, i.e.,

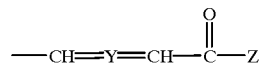

and Y is

wherein $R_5$ is a bond, i.e., Y is

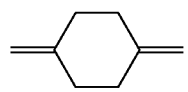

and Z is OH or $OR_7$

Typically T represents:

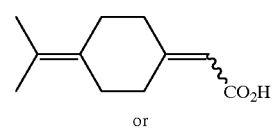

or

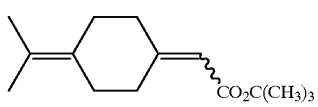

Representative compounds of the invention include compounds of the formula:

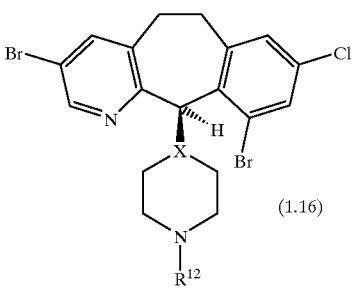

(1.16)

wherein $R^{12}$ is selected from:
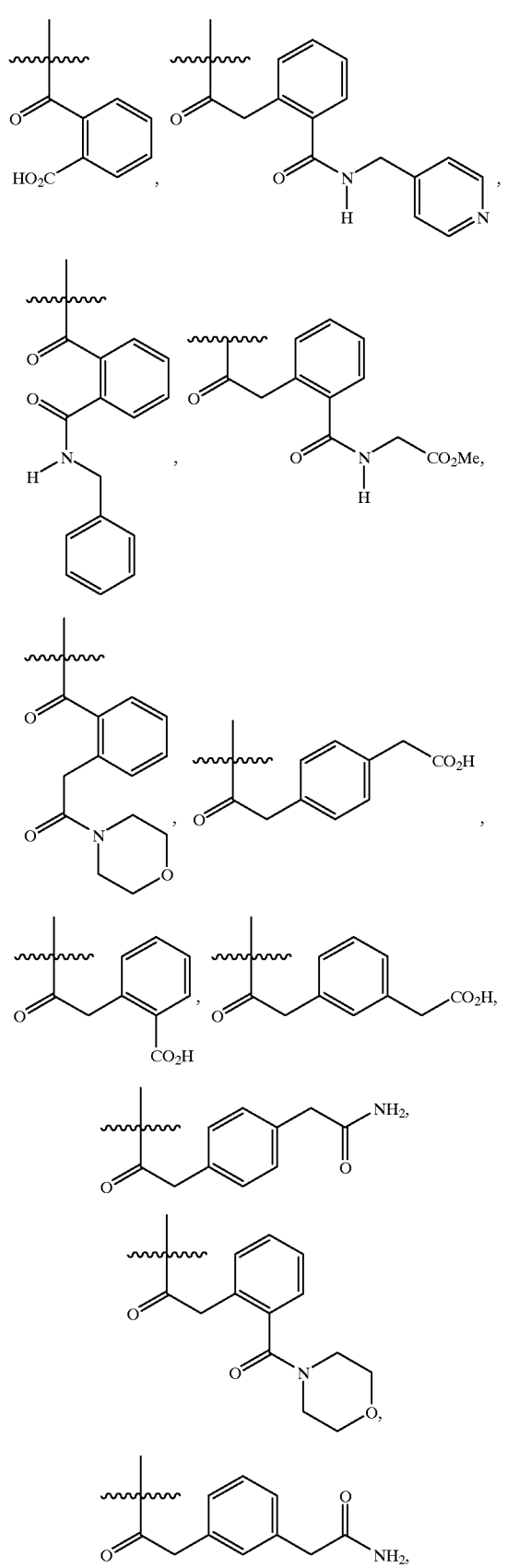
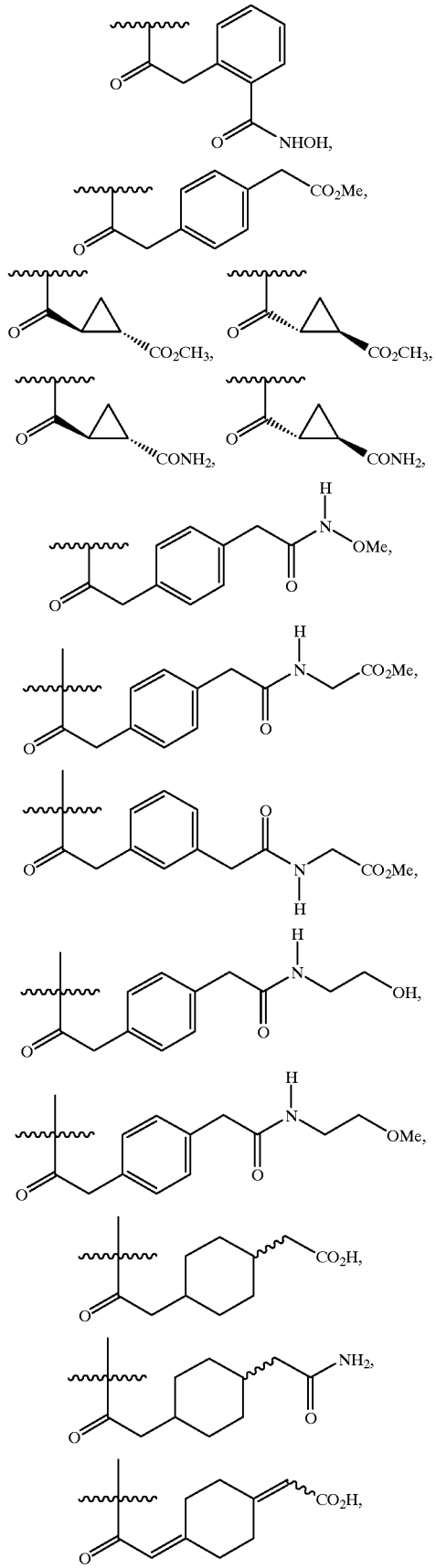

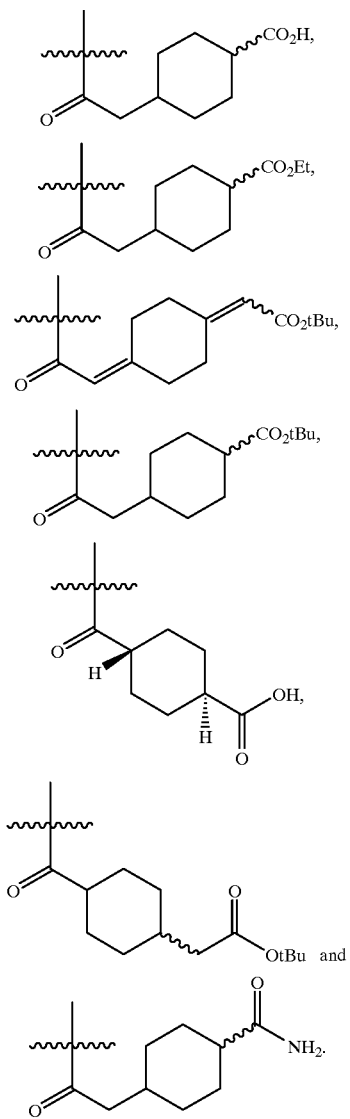

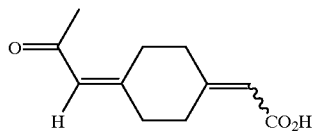

both E and Z isomers are contemplated, i.e.,

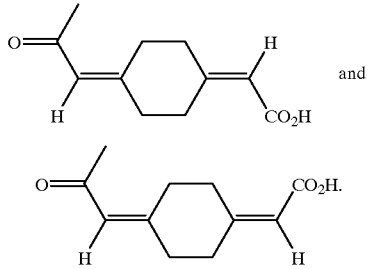

When T equals

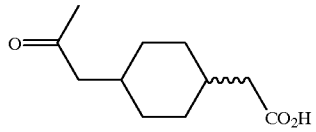

both isomers are contemplated i.e.,

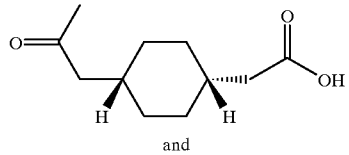

and

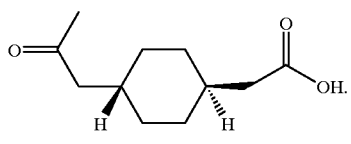

Those skilled in the art will appreciate that substituent $R^{12}$ is the same as substituent

in Formula 1.0.

Lines drawn into the ring systems indicate that the indicates bond may be attached to any of the substitutable ring carbon atoms.

Bonds drawn with a wavy line (∿∿∿) indicates that the bond may be attached to either position in carbon. For example, in T equal to The term $(C_1-C_6)$alkyl as used herein means straight and branched chain alkyl groups of one to six carbons including methyl, ethyl, propyl, iso-propyl, butyl, sec-butyl, iso-butyl, tert-butyl, pentyl, iso-pentyl, neo-pentyl and hexyl groups.

The term $(C_1-C_6)$alkyl substituted by $OR_5$, $COR_5$, phenyl or heteroaryl include straight and branded chain alkyl groups and typically include —$CH_2OR_5$, —$CH_2C_6H_5$, —$CH_2COR_5$ or

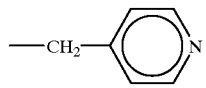

wherein $R_5$ is $(C_1-C_6)$alkyl such as tert-butyl.

The term $(C_1-C_6)$alkanoyl as used herein means straight and branched chain alkanoyl groups of one to six carbons including formyl, acetyl, propanoyl, butanoyl, 2-methylpropanoyl, pentanoyl, 3-methylbutanoyl, hexanoyl, and 4 methylpentanoyl.

The term $(C_1-C_6)$perhaloalkyl as used herein means straight and branched chain alkyl groups of one to six carbons wherein the H atoms are replaced by halo which is preferably F or Cl.

Certain compounds of the invention may exist in different isomeric (e.g., enantiomers and diastereoisomers) forms. The invention contemplates all such isomers both in pure form and in admixture, including racemic mixtures. Enol forms are also included.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyridonitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of the invention may be prepared according to the procedures described in WO 95/10516 published Apr. 20, 1995, U.S. Pat. No. 5,719,148 issued Feb. 17, 1998 and copending application Ser. No. 08/766,601 filed Dec. 12, 1996; the disclosures of each being incorporated herein by reference thereto; and according to the procedures described below.

Compounds of the invention can be prepared according to the reaction:

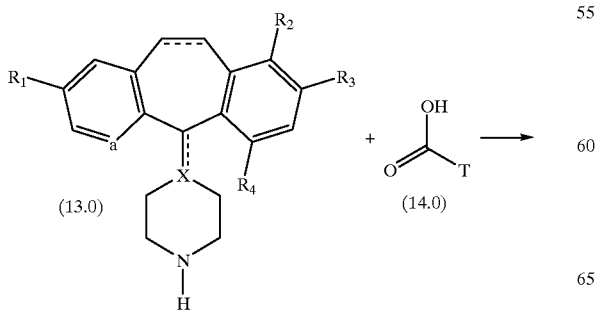

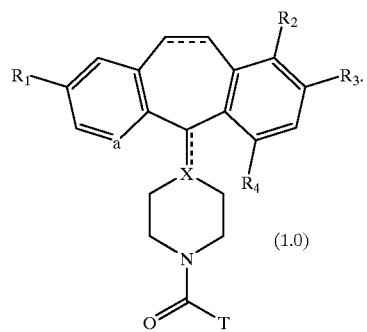

In the reaction, the cyclic ether carboxylic acid (14.0) is coupled to the tricyclic amine (14.0) using amide bond forming conditions well known to those skilled in the art. The substituents are as defined for Formula 1.0. For example, carbodiimide coupling methods (e.g., DEC) can be used. For example, the carboxylic acid (14.0) can be reacted with the tricyclic amine (13.0) using DEC/HOBT/NMM in DMF at about 25° C. for a sufficient period of time, e.g., about 18 hours, to produce a compound of Formula 1.0.

For example, using the carbodiimide coupling methods, compounds of the invention can be produced according to the reaction:

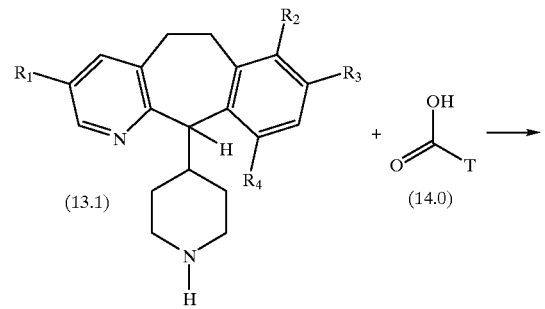

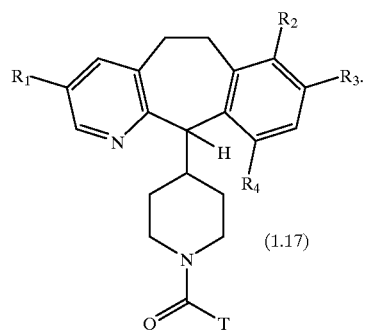

Compounds of Formula 13.0a

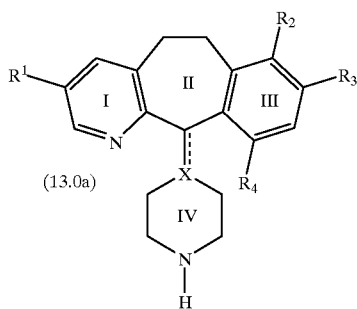

(13.0a)

are prepared by methods known in the art, for example by methods disclosed in WO 95/10516, in U.S. Pat. No. 5,151,423 and those described below. Compounds of Formula 13.0a wherein X is C (when the double bond is present) or CH and the C-3 postion of the pyridine ring in the tricyclic structure is substituted by bromo (i.e., $R^1$ is Br) can also be prepared by a procedure comprising the following steps:

(a) reacting an amide of the formula

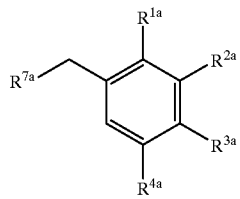

wherein $R^{11a}$ is Br, $R^{5a}$ is hydrogen and $R^{6a}$ is $(C_1-C_6)$ alkyl, aryl or heteroaryl; $R^{5a}$ is $(C_1-C_6)$alkyl, aryl or heteroaryl and $R^{6a}$ is hydrogen; $R^{5a}$ and $R^{6a}$ are independently selected from the group consisting of $(C_1-C_6)$alkyl and aryl; or $R^{5a}$ and $R^{6a}$, together with the nitrogen to which they are attached, form a ring comprising 4 to 6 carbon atoms or comprising 3 to 5 carbon atoms and one hetero moiety selected from the group consisting of —O— and —$NR^{9a}$—, wherein $R^{9a}$ is H, $(C_1-C_6)$alkyl or phenyl;

with a compound of the formula

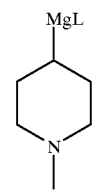

wherein $R^{1a}$, $R^{2a}$, $R^{3a}$ and $R^{4a}$ are are independently selected from the group consisting of hydrogen and halo and $R^{7a}$ is Cl or Br, in the presence of a strong base to obtain a compound of the formula

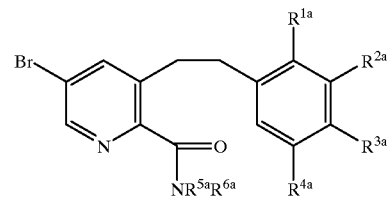

(b) reacting a compound of step (a) with
(i) $POCl_3$ to obtain a cyano compound of the formula

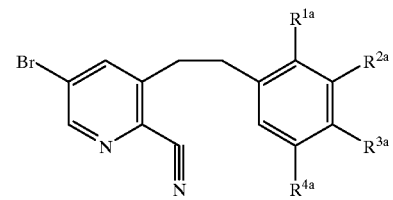

(ii) DIBALH to obtain an aldehyde of the formula

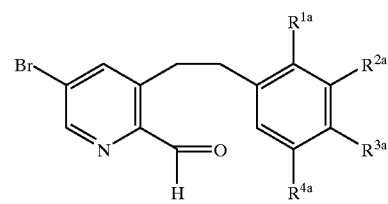

(c) reacting the cyano compound or the aldehyde with a piperidine derivative of the formula wherein L is a leaving group selected from the group consisting of Cl and Br, to obtain a ketone or an alcohol of the formula below, respectively:

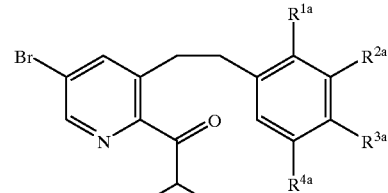

or

-continued

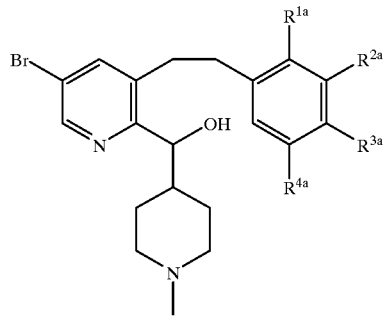

(d)(i) cyclizing the ketone with $CF_3SO_3H$ to obtain a compound of Formula 13.0a wherein the dotted line represents a double bond; or (d)(ii) cyclizing the alcohol with polyphosphoric acid to obtain a compound of Formula 13.0a wherein the dotted line represents a single bond.

Methods for preparing compounds of Formula 13.0a disclosed in WO 95/10516, U.S. Pat. No. 5,151,423 and described below employ a tricyclic ketone intermediate. Such intermediates of the formula

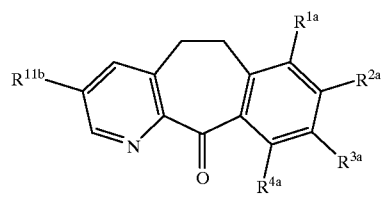

wherein $R^{11b}$, $R^{1a}$, $R^{2a}$, $R^{3a}$ and $R^{4a}$ are independently selected from the group consisting of hydrogen and halo, can be prepared by the following process comprising:

(a) reacting a compound of the formula

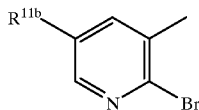

(i) with an amine of the formula $NHR^{5a}R^{6a}$, wherein $R^{5a}$ and $R^{6a}$ are as defined in the process above; in the presence of a palladium catalyst and carbon monoxide to obtain an amide of the formula:

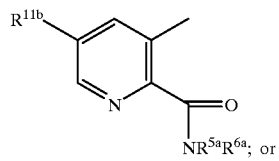

(ii) with an alcohol of the formula $R^{10a}OH$, wherein $R^{10a}$ is $(C_1-C_6)$ lower alkyl or $C_3-C_6$ cycloalkyl, in the presence of a palladium catalyst and carbon monoxide to obtain the ester of the formula

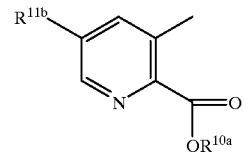

followed by reacting the ester with an amine of formula $NHR^{5a}R^{6a}$ to obtain the amide;

(b) reacting the amide with an iodo-substituted benzyl compound of the formula

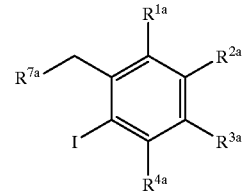

wherein $R^{1a}$, $R^{2a}$, $R^{3a}$, $R^{4a}$ and $R^{7a}$ are as defined above, in the presence of a strong base to obtain a compound of the formula

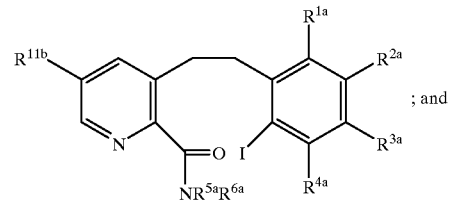

; and (c) cyclizing a compound of step (b) with a reagent of the formula $R^{8a}MgL$, wherein $R^{8a}$ is $C_1-C_8$ alkyl, aryl or heteroaryl and L is Br or Cl, provided that prior to cyclization, compounds wherein $R^{5a}$ or $R^{6a}$ is hydrogen are reacted with a suitable N-protecting group.

Compounds of Formula 1.0, wherein substituent a is NO (Ring I) and X is CH, can be made from compounds of Formula 13.0a using procedures well known to those skilled in the art. For example the compound of Formula 13.0a can be reacted with m-chloroperoxybenzoic acid in a suitable organic solvent, e.g., dichloromethane (usually anhydrous) or methylene chloride, at a suitable temperature, to produce a compound of Formula 13.0b

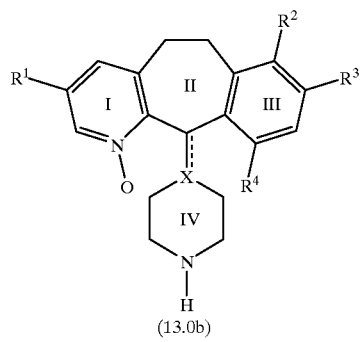

(13.0b)

Generally, the organic solvent solution of Formula 13.0a is cooled to about 0° C. before the m-chloroperoxybenzoic acid is added. The reaction is then allowed to warm to room temperature during the reaction period. The desired product can be recovered by standard separation means. For example, the reaction mixture can be washed with an aqueous solution of a suitable base, e.g., saturated sodium bicarbonate or NaOH (e.g., 1N NaOH), and then dried over anhydrous magnesium sulfate. The solution containing the product can be concentrated in vacuo. The product can be purified by standard means, e.g., by chromatography using silica gel (e.g., flash column chromatography).

Alternatively, compounds of Formula 1.0, wherein substituent a is NO and X is C or CH, can be made from compounds of Formula 1.0, wherein substituent a is N, by the m-chloroperoxybenzoic acid oxidation procedure described above.

Also, alternatively, the compounds of Formula 1.0, wherein substituent a is NO and X is C or CH, can be made from tricyclic ketone compounds

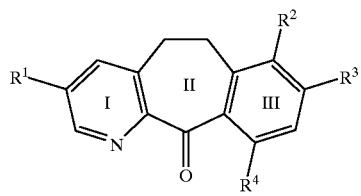

(I)

using the oxidation procedure with m-chloroperoxybenzoic acid. The oxidized intermediate compounds

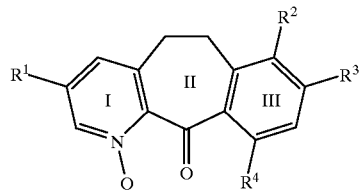

(II)

are then reacted by methods known in the art to produce compounds of the invention.

Those skilled in the art will appreciate that the oxidation reaction can be conducted on racemic mixtures and the isomers can then be separated by know techniques, or the isomers can be separated first and then oxidized to the corresponding N-oxide.

Those skilled in the art will appreciate that it is preferable to avoid an excess of m-chloroperoxybenzoic acid when the oxidation reaction is carried out on the compounds having a C-11 double bond to piperidine Ring IV. In these reactions an excess of m-chloroperoxybenzoic acid can cause epoxidation of the C-11 double bond.

(+)-Isomers of compounds of formula 13.0 wherein X is CH can be prepared with high enantioselectivity by using a process comprising enzyme catalyzed transesterification. Preferably, a racemic compound of formula 13.0, wherein X is C, the double bond is present and $R^4$ is not H, is reacted with an enzyme such as Toyobo LIP-300 and an acylating agent such as trifluoroethly isobutyrate; the resultant (+)-amide is then hydrolyzed, for example by refluxing with an acid such as $H_2SO_4$, to obtain the corresponding optically enriched (+)-isomer wherein X is CH and $R^3$ is not H. Alternatively, a racemic compound of formula II, wherein X is C, the double bond is present and $R^4$ is not H, is first reduced to the corresponding racemic compound of formula II wherein X is CH and then treated with the enzyme (Toyobo LIP-300) and acylating agent as described above to obtain the (+)-amide, which is hydrolyzed to obtain the optically enriched (+)-isomer.

Compounds of the invention, wherein a is NO and X is N, can be prepared from the tricyclic ketone (II) described above. Ketone (II) can be converted to the corresponding C-11 hydroxy compound which in turn can be converted to the corresponding C-11 chloro compound

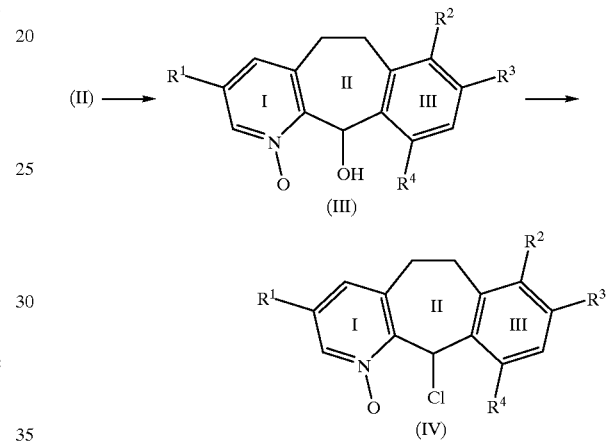

and (IV) can then be reacted with piperazine to produce the intermediate

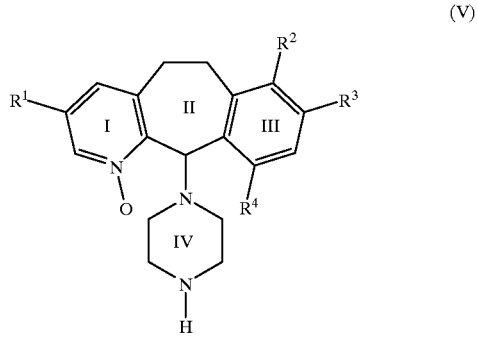

(V)

Intermediate (V) can then be reacted with the reagents, using techniques well known in the art, which will provide the desired compound.

In general, the compounds to this invention are prepared as shown in the example in Scheme 1 using standard coupling conditions (DEC, HOBT, N-methylmorpholine). In all cases the amine is as prepared in Preparative Example 6 and commercially available or later described carboxylic acids of formula 14.0 are used.

SCHEME 1

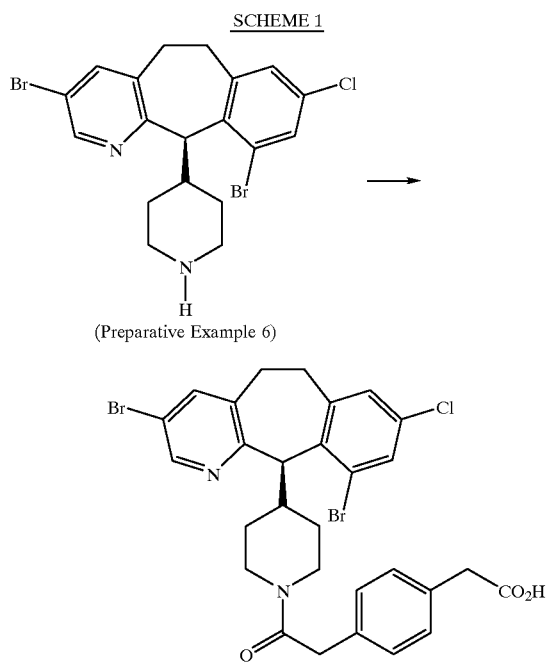

(Preparative Example 6)

The cycloakyldiacetic acid derivatives (formula 14.0 wherein T is as described as hereinabove and a and b are 1 and $R_5$ is H) can be prepared starting from the commercially available diketone or monoketal of the desired cycloalkyl derivative as shown in Scheme 2 where n=1 or 2. In all cases the compounds were tested as a mixture of cis/trans isomers unless otherwise indicated.

SCHEME 2

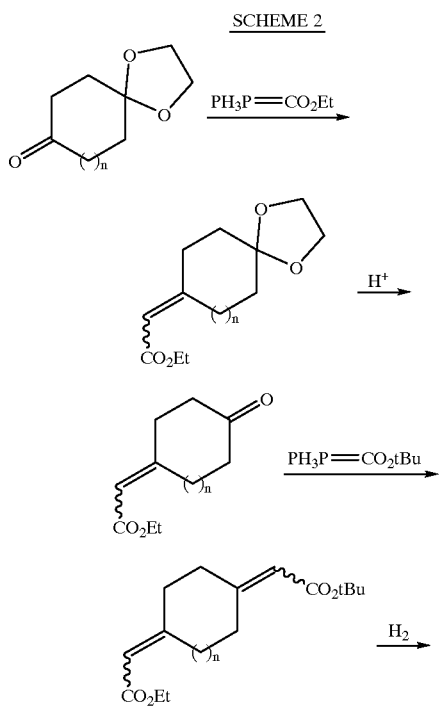

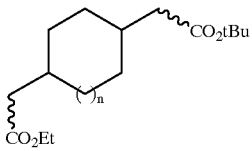

The synthesis of the 4-carboxy cycloalkylacetic acids (X wherein b is 1, c is 0 and $R_5$ is H) can be carried out in a similar fashion from commercially available ethyl 4-oxocyclohexane carboxylate as shown in Scheme 3 and 1,3-cyclopentanedione monoketal as shown in Scheme 4.

SCHEME 3

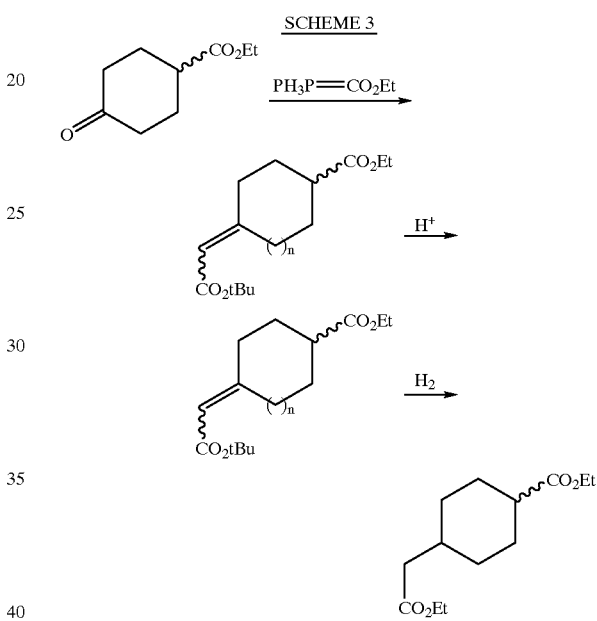

SCHEME 4

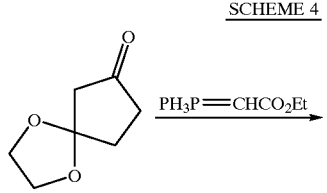

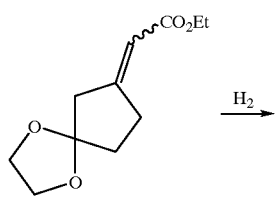

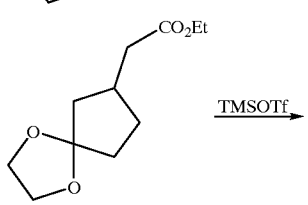

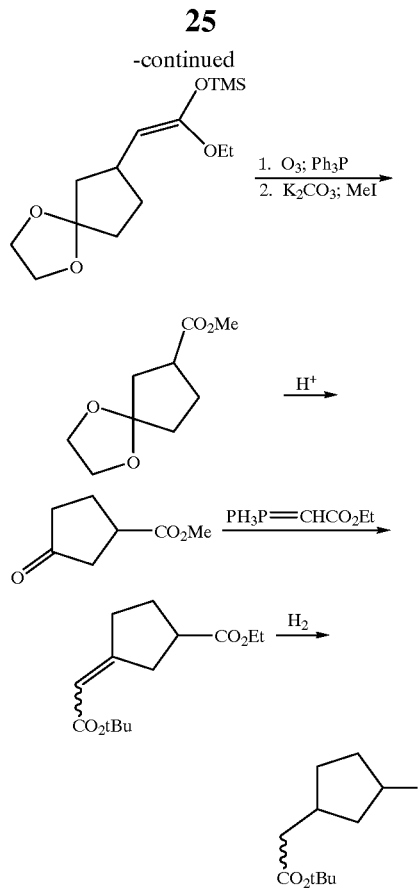

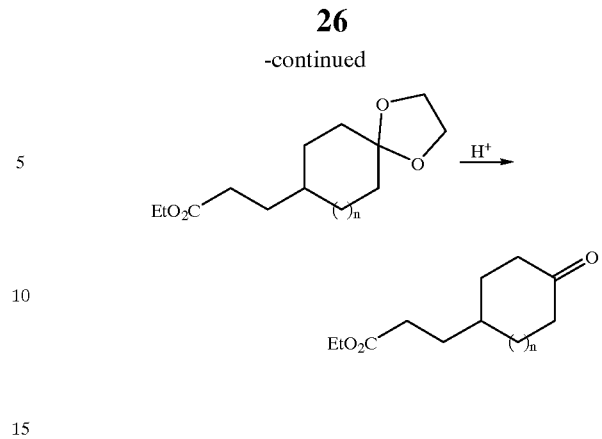

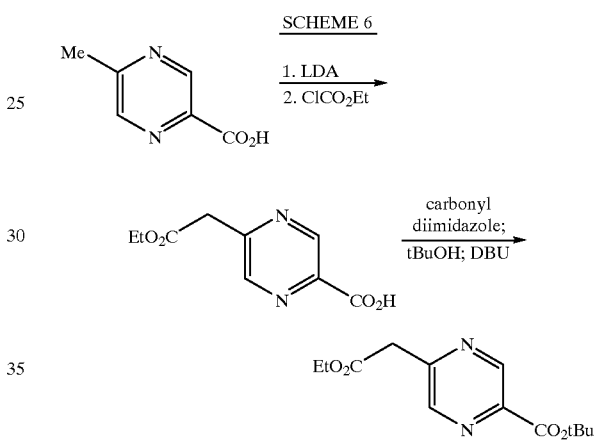

In both cases, selective hydrolysis of either the t-butyl or alkyl ester can be carried out for coupling as shown in Scheme 1 to give compounds with or without a methylene spacer between the amide and the cycloalkyl portion of the molecule.

The derivatives wherein X, b and/or c=3 can be constructed starting with similar precursors as in the above examples (Scheme 5). From the ketone, similar synthetic methodology well known to those skilled in the art can be used to put together the rest of the compound, depending on whether and acetic acid (b=2) derivative or carboxy (b=0) derivative is desired.

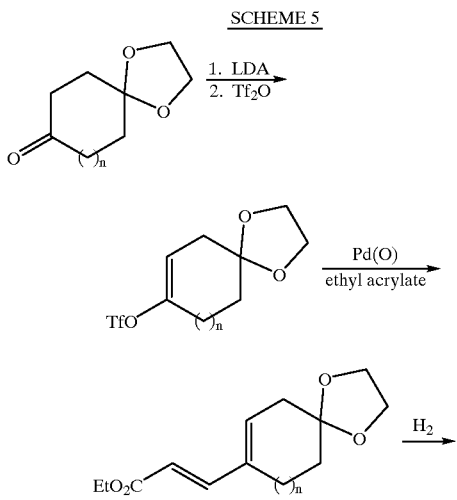

The pyrazine 4-carboxy acetic acids and 1,4-diacetic acids can be prepared as shown in Scheme 6 and Scheme 7, respectively from commercially avaiable 5-methylpyrazine-2-carboxylic acid and 2,5-dimethyl pyrazine respectively:

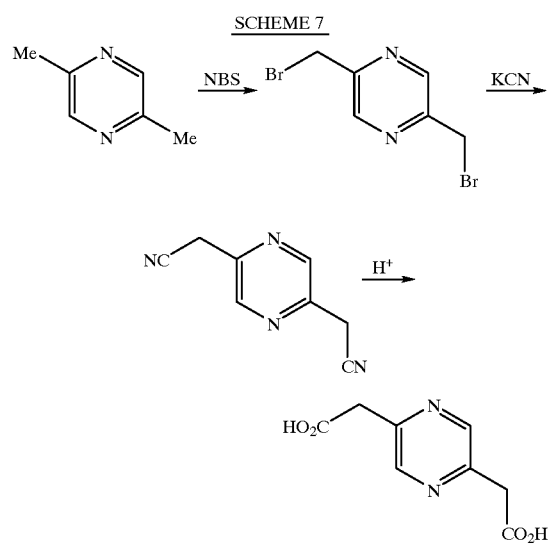

Compounds useful in this invention are exemplified by the following examples, which should not be construed to limit the scope of the disclosure.

PREPARATIVE EXAMPLE 1

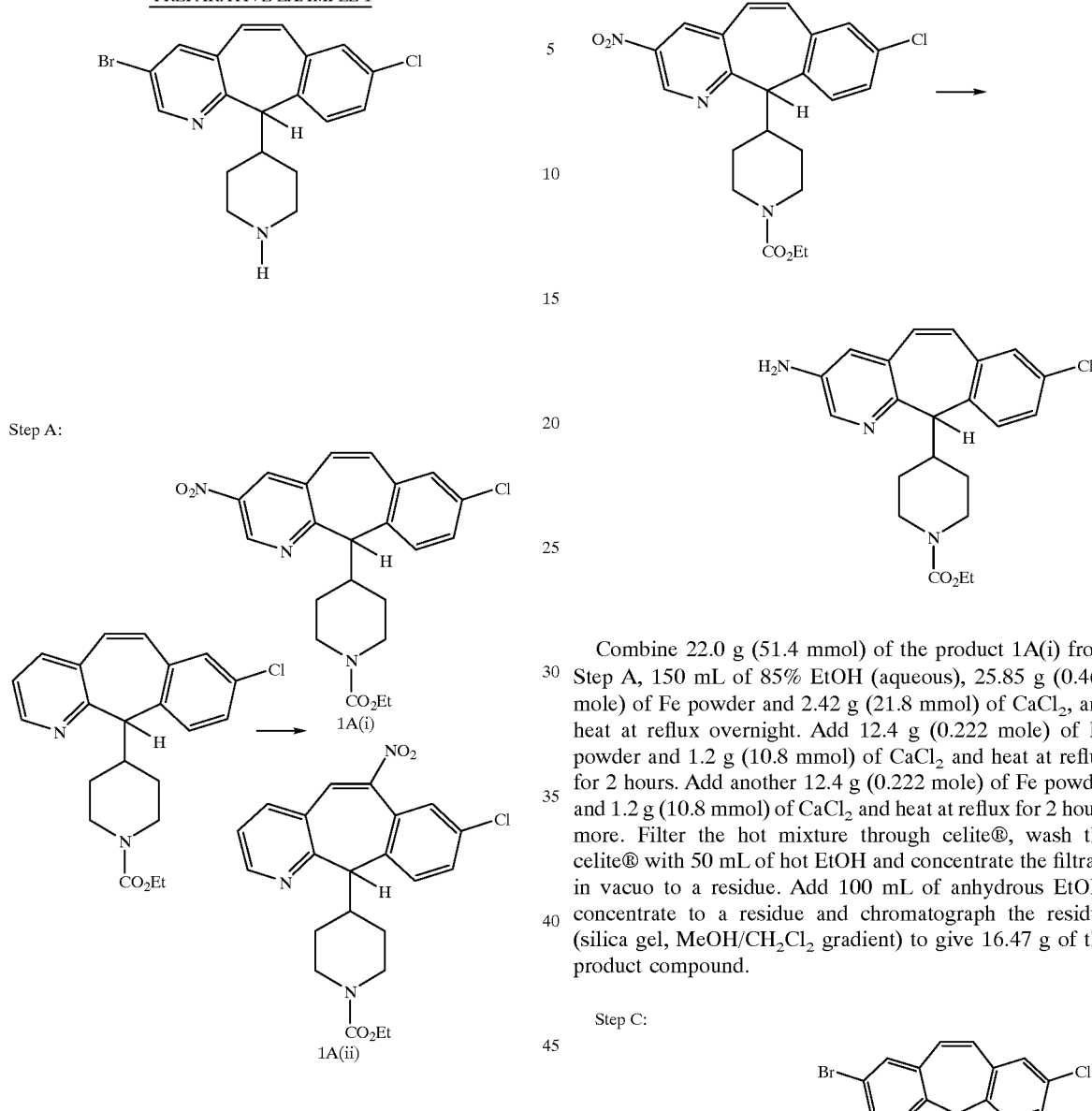

Step A:

Combine 14.95 g (39 mmol) of 8-chloro-11-(1-ethoxycarbonyl-4-piperidinyl)-11 H-benzo[5,6]cyclohepta[1,2-b]pyridine and 150 mL of $CH_2Cl_2$, then add 13.07 g (42.9 mmol) of $(nBu)_4NNO_3$ and cool the mixture to 0° C. Slowly add (dropwise) a solution of 6.09 mL (42.9 mmol) of TFAA in 20 mL of $CH_2Cl_2$ over 1.5 hours. Keep the mixture at 0° C. overnight, then wash successively with saturated $NaHCO_3$ (aqueous), water and brine. Dry the organic solution over $Na_2SO_4$, concentrate in vacuo to a residue and chromatograph the residue (silica gel, EtOAc/hexane gradient) to give 4.32 g and 1.90 g of the two product compounds 1A(i) and 1A(ii), respectively. Mass Spec. for compound 1A(i): $MH^+$=428.2. Mass Spec. for compound 1A(ii): $MH^+$=428.3.

Step B:

Combine 22.0 g (51.4 mmol) of the product 1A(i) from Step A, 150 mL of 85% EtOH (aqueous), 25.85 g (0.463 mole) of Fe powder and 2.42 g (21.8 mmol) of $CaCl_2$, and heat at reflux overnight. Add 12.4 g (0.222 mole) of Fe powder and 1.2 g (10.8 mmol) of $CaCl_2$ and heat at reflux for 2 hours. Add another 12.4 g (0.222 mole) of Fe powder and 1.2 g (10.8 mmol) of $CaCl_2$ and heat at reflux for 2 hours more. Filter the hot mixture through celite®, wash the celite® with 50 mL of hot EtOH and concentrate the filtrate in vacuo to a residue. Add 100 mL of anhydrous EtOH, concentrate to a residue and chromatograph the residue (silica gel, MeOH/$CH_2Cl_2$ gradient) to give 16.47 g of the product compound.

Step C:

Combine 16.47 g (41.4 mmol) of the product from Step B, and 150 mL of 48% HBr (aqueous) and cool to −3° C. Slowly add (dropwise) 18 mL of bromine, then slowly add (dropwise) a solution of 8.55 g (0.124 mole) of NaNO₂ in 85 mL of water. Stir for 45 minutes at −3° to 0° C., then adjust to pH=10 by adding 50% NaOH (aqueous). Extract with EtOAc, wash the extracts with brine and dry the extracts over Na₂SO₄. Concentrate to a residue and chromatograph (silica gel, EtOAc/hexane gradient) to give 10.6 g and 3.28 g of the two product compounds 1C(i) and 1C(ii), respectively. Mass Spec. for compound 1C(i): MH⁺=461.2. Mass Spec. for compound 1C(ii): MH⁺=539.

Step D:

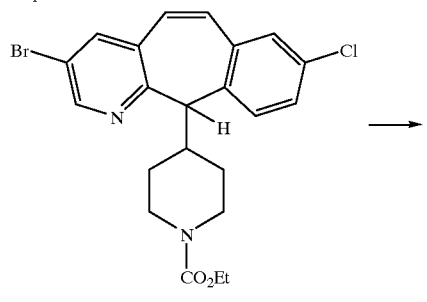

Hydrolyze the product 3C(i) of Step C by dissolving in concentrated HCl and heating to about 100° C. for @16 hours. Cool the mixture, the neutralize with 1 M NaOH (aqueous). Extract with CH₂Cl₂, dry the extracts over MgSO₄, filter and concentrate in vacuo to the title compound. Mass Spec.: MH⁺=466.9.

PREPARATIVE EXAMPLE 2

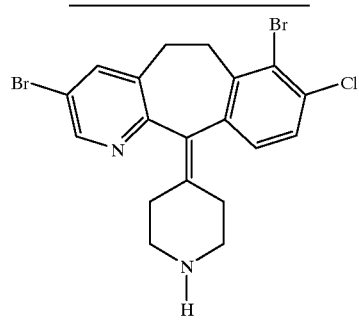

Step A:

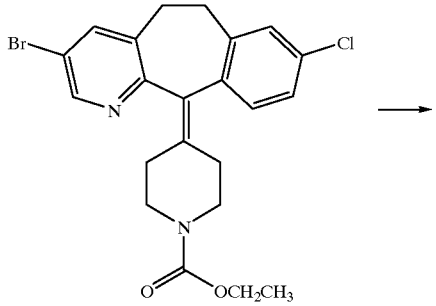

Combine 25.86 g (55.9 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 250 mL of concentrated H₂SO₄ at −5° C., then add 4.8 g (56.4 mmol) of NaNO₃ and stir for 2 hours. Pour the mixture into 600 g of ice and basify with concentrated NH₄OH (aqueous). Filter the mixture, wash with 300 mL of water, then extract with 500 mL of CH₂Cl₂. Wash the extract with 200 mL of water, dry over MgSO₄, then filter and concentrate in vacuo to a residue. Chromatograph the residue (silica gel, 10% EtOAc/CH₂Cl₂) to give 24.4 g (86% yield) of the product. m.p.=165–167° C., Mass Spec.: MH⁺=506 (CI). Elemental analysis: calculated—C, 52.13; H, 4.17; N, 8.29; found—C, 52.18; H, 4.51; N, 8.16.

Step B:

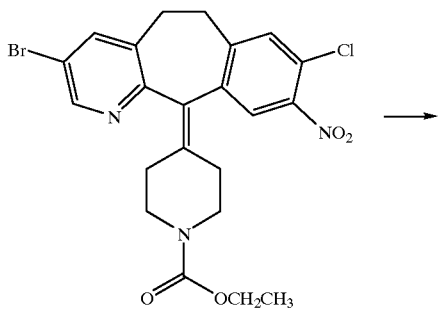

-continued

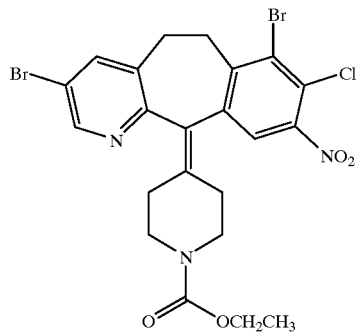

Combine 20 g (40.5 mmol) of the product of Step A and 200 mL of concentrated H₂SO₄ at 20° C., then cool the mixture to 0° C. Add 7.12 g (24.89 mmol) of 1,3-dibromo-5,5-dimethyl-hydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated NH₄OH (aqueous) at 0° C., and collect the resulting solid by filtration. Wash the solid with 300 mL of water, slurry in 200 mL of acetone and filter to provide 19.79 g (85.6% yield) of the product. m.p.=236–237° C., Mass Spec.: MH⁺=584 (CI). Elemental analysis: calculated—C, 45.11; H, 3.44; N, 7.17; found—C, 44.95; H, 3.57; N, 7.16

Step C:

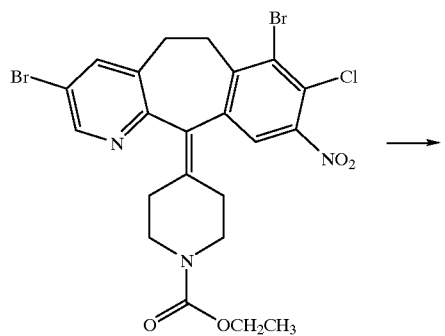

Combine 25 g (447 mmol) of Fe filings, 10 g (90 mmol) of CaCl₂ and a suspension of 20 g (34.19 mmol) of the product of Step B in 700 mL of 90:10 EtOH/water at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of CH₂Cl₂, wash with 300 mL of water and dry over MgSO₄. Filter and concentrate in vacuo to a residue, then chromatograph (silica gel, 30% EtOAc/CH₂Cl₂) to give 11.4 g (60% yield) of the product. m.p.=211–212° C., Mass Spec.: MH⁺=554 (CI). Elemental analysis: calculated—C, 47.55; H, 3.99; N, 7.56; found—C, 47.45; H, 4.31; N, 7.49.

Step D:

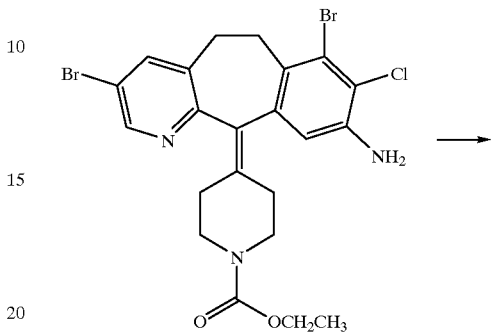

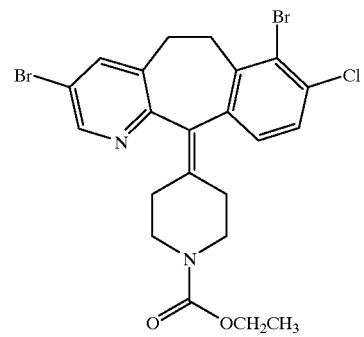

Slowly add (in portions) 20 g (35.9 mmol) of the product of Step C to a solution of 8 g (116 mmol) of NaNO₂ in 120 mL of concentrated HCl (aqueous) at −10° C. Stir the resulting mixture at 0° C. for 2 hours, then slowly add (dropwise) 150 mL (1.44 mole) of 50% H₃PO₂ at 0° C. over a 1 hour period. Stir at 0° C. for 3 hours, then pour into 600 g of ice and basify with concentrated NH₄OH (aqueous). Extract with 26×300 mL of CH₂Cl₂, dry the extracts over MgSO₄, then filter and concentrate in vacuo to a residue. Chromatograph the residue (silica gel, 25% EtOAc/hexanes) to give 13.67 g (70% yield) of the product. m.p.=163–165° C., Mass Spec.: MH⁺=539 (CI). Elemental analysis: calculated—C, 48.97; H, 4.05; N, 5.22; found—C, 48.86; H, 3.91; N, 5.18.

Step E:

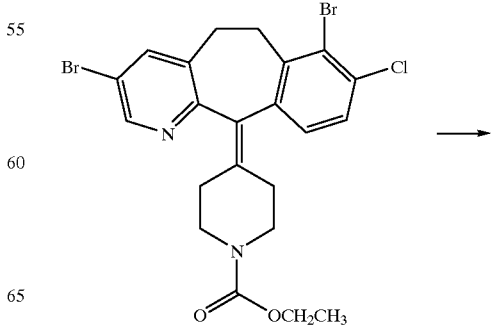

-continued

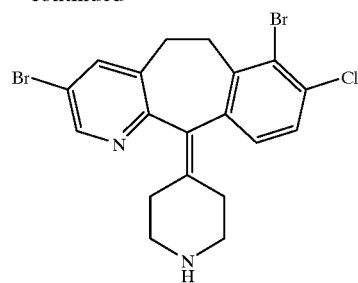

Combine 6.8 g (12.59 mmol) of the product of Step D and 100 mL of concentrated HCl (aqueous) and stir at 85° C. overnight. Cool the mixture, pour it into 300 g of ice and basify with concentrated NH$_4$OH (aqueous). Extract with 2×300 mL of CH$_2$Cl$_2$, then dry the extracts over MgSO$_4$. Filter, concentrate in vacuo to a residue, then chromatograph (silica gel, 10% MeOH/EtOAc+2% NH$_4$OH (aqueous)) to give 5.4 g (92% yield) of the title compound. m.p.= 172–174° C., Mass Spec.: MH$^+$=467 (FAB). Elemental analysis: calculated—C, 48.69; H, 3.65; N, 5.97; found—C, 48.83; H, 3.80; N, 5.97

PREPARATIVE EXAMPLE 3

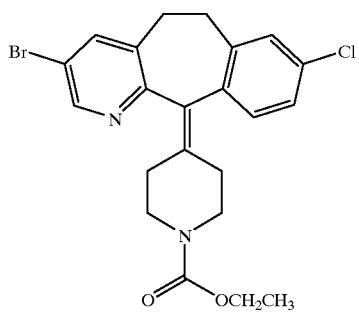

Step A:

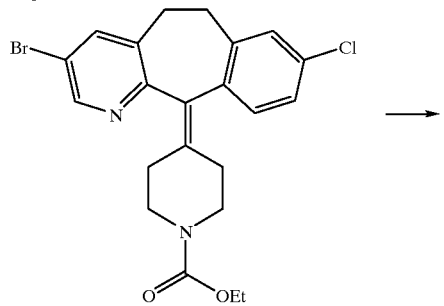

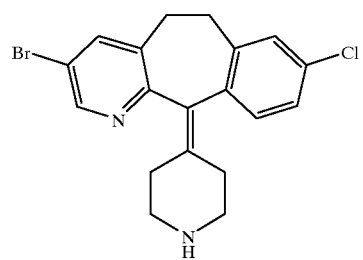

Hydrolyze 2.42 g of 4-(8-chloro-3-bromo-5,6-dihydro-11H-benzo[5,6]cyclohepta[1,2-b]pyridin-11-ylidene)-1-piperidine-1-carboxylic acid ethyl ester via substantially the same procedure as described in Preparative Example 1, Step D, to give 1.39 g (69% yield) of the product.

Step B:

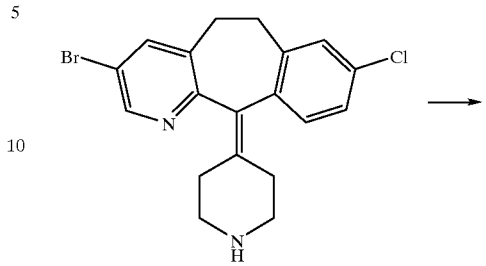

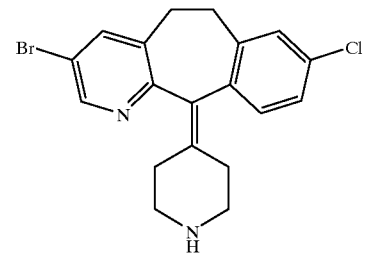

Combine 1 g (2.48 mmol) of the product of Step A and 25 mL of dry toluene, add 2.5 mL of 1 M DIBAL in toluene and heat the mixture at reflux. After 0.5 hours, add another 2.5 mL of 1 M DIBAL in toluene and heat at reflux for 1 hour. (The reaction is monitored by TLC using 50% MeOH/CH$_2$Cl$_2$+NH$_4$OH (aqueous).) Cool the mixture to room temperature, add 50 mL of 1 N HCl (aqueous) and stir for 5 min. Add 100 mL of 1 N NaOH (aqueous), then extract with EtOAc (3×150 mL). Dry the extracts over MgSO$_4$, filter and concentrate in vacuo to give 1.1 g of the title compound.

PREPARATIVE EXAMPLE 4

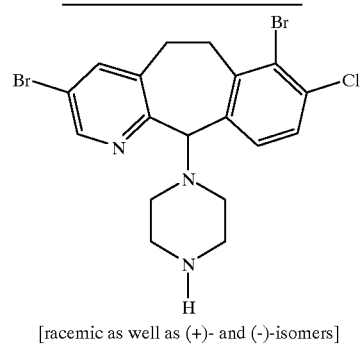

[racemic as well as (+)- and (-)-isomers]

Step A:

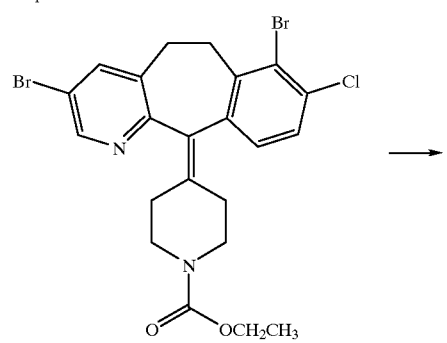

Combine 16.6 g (0.03 mole) of the product of Preparative Example 2, Step D, with a 3:1 solution of CH₃CN and water (212.65 mL CH₃CN and 70.8 mL of water) and stir the resulting slurry overnight at room temperature. Add 32.833 g (0.153 mole) of NaIO₄ and then 0.31 g (2.30 mmol) of RuO₂ and stir at room temperature give 1.39 g (69% yield) of the product. (The addition of RuO is accompanied by an exothermic reaction and the temperature climbs from 20° to 30° C.) Stir the mixture for 1.3 hrs. (temperature returned to 25° C. after about 30 min.), then filter to remove the solids and wash the solids with CH₂Cl₂. Concentrate the filtrate in vacuo to a residue and dissolve the residue in CH₂Cl₂. Filter to remove insoluble solids and wash the solids with CH₂Cl₂. Wash the filtrate with water, concentrate to a volume of about 200 mL and wash with bleach, then with water. Extract with 6 N HCl (aqueous). Cool the aqueous extract to 0° C. and slowly add 50% NaOH (aqueous) to adjust to pH=4 while keeping the temperature <30° C. Extract twice with CH₂Cl₂, dry over MgSO₄ and concentrate in vacuo to a residue. Slurry the residue in 20 mL of EtOH and cool to 0° C. Collect the resulting solids by filtration and dry the solids in vacuo to give 7.95 g of the product. $^1$H NMR (CDCl₃, 200 MHz): 8.7 (s, 1H); 7.85 (m, 6H); 7.5 (d, 2H); 3.45 (m, 2H); 3.15 (m, 2H).

Step B:

Combine 21.58 g (53.75 mmol) of the product of Step A and 500 mL of an anhydrous 1:1 mixture of EtOH and toluene, add 1.43 g (37.8 mmol) of NaBH₄ and heat the mixture at reflux for 10 min. Cool the mixture to 0° C., add 100 mL of water, then adjust to pH≈4–5 with 1 M HCl (aqueous) while keeping the temperature <10° C. Add 250 mL of EtOAc and separate the layers. Wash the organic layer with brine (3×50 mL) then dry over Na₂SO₄. Concentrate in vacuo to a residue (24.01 g) and chromatograph the residue (silica gel, 30% hexane/CH₂Cl₂) to give the product. Impure fractions were purified by rechromatography. A total of 18.57 g of the product was obtained. $^1$H NMR (DMSO-d₆, 400 MHz): 8.5 (s, 1H); 7.9 (s, 1H); 7.5 (d of d, 2H); 6.2 (s, 1H); 6.1 (s, 1H); 3.5 (m, 1H); 3.4 (m, 1H); 3.2 (m, 2H).

Step C:

Combine 18.57 g (46.02 mmol) of the product of Step B and 500 mL of CHCl₃, then add 6.70 mL (91.2 mmol) of SOCl₂, and stir the mixture at room temperature for 4 hrs. Add a solution of 35.6 g (0.413 mole) of piperazine in 800 mL of THF over a period of 5 min. and stir the mixture for 1 hr. at room temperature. Heat the mixture at reflux overnight, then cool to room temperature and dilute the mixture with 1 L of CH₂Cl₂. Wash with water (5×200 mL), and extract the aqueous wash with CHCl₃ (3×100 mL). Combine all of the organic solutions, wash with brine (3×200 mL) and dry over MgSO₄. Concentrate in vacuo to a residue and chromatograph (silica gel, gradient of 5%, 7.5%, 10% MeOH/CH₂Cl₂+NH₄OH) to give 18.49 g of the title compound as a racemic mixture.

Step D - Separation of Enantiomers:

The racemic title compound of Step C is separated by it preparative chiral chromatography (Chiralpack AD, 5 cm×50 cm column, flow rate 100 mL/min., 20% iPrOH/hexane+0.2% diethylamine), to give 9.14 g of the (+)-isomer and 9.30 g of the (−)-isomer.

Physical chemical data for (+)-isomer: m.p.=74.5°–77.5° C.; Mass Spec. MH⁺=471.9; [α]=+97.4° (8.48 mg/2 mL MeOH).

Physical chemical data for (−)-isomer: m.p.=82.9°–84.5° C.; Mass Spec. MH⁺=471.8; [α]=−97.4° (8.32 mg/2 mL MeOH).

PREPARATIVE EXAMPLE 5

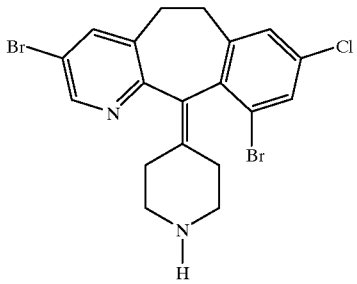

Step A:

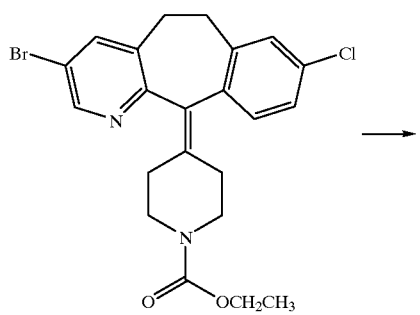

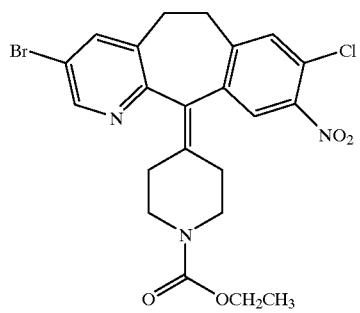

Combine 15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 150 mL of concentrated $H_2SO_4$ at $-5°$ C., then add 3.89 g (38.5 mmol) of $KNO_3$ and stir for 4 hours. Pour the mixture into 3 L of ice and basify with 50% NaOH (aqueous). Extract with $CH_2Cl_2$, dry over $MgSO_4$, then filter and concentrate in vacuo to a residue. Recrystallize the residue from acetone to give 6.69 g of the product. $^1$H NMR (CDCl$_3$, 200 MHz): 8.5 (s, 1H); 7.75 (s, 1H); 7.6 (s, 1H); 7.35 (s, 1H); 4.15 (q, 2H); 3.8 (m, 2H); 3.5–3.1 (m, 4H); 3.0–2.8 (m, 2H); 2.6–2.2 (m, 4H); 1.25 (t, 3H).

Step B:

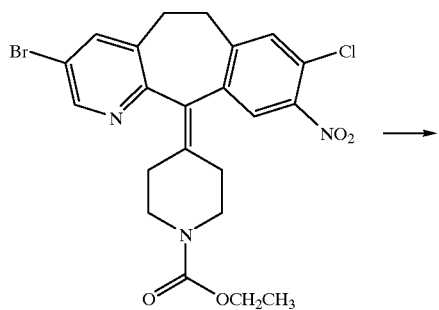

-continued

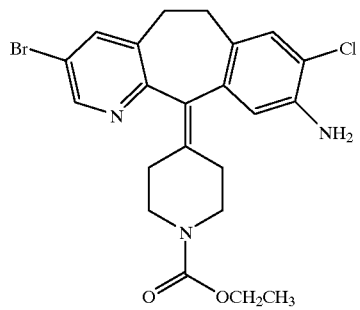

Combine 6.69 g (13.1 mmol) of the product of Step A and 100 mL of 85% EtOH/water, then add 0.66 g (5.9 mmol) of $CaCl_2$ and 6.56 g (117.9 mmol) of Fe and heat the mixture at reflux overnight. Filter the hot reaction mixture through celite® and rinse the filter cake with hot EtOH. Concentrate the filtrate in vacuo to give 7.72 g of the product. Mass Spec.: MH$^+$=478.0

Step C:

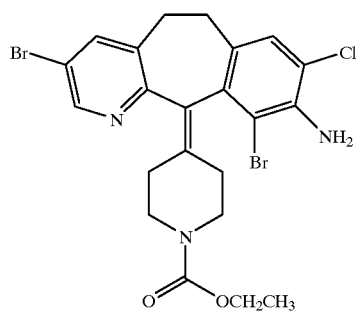

Combine 7.70 g of the product of Step B and 35 mL of HOAc, then add 45 mL of a solution of $Br_2$ in HOAc and stir the mixture at room temperature overnight. Add 300 mL of 1 N NaOH (aqueous), then 75 mL of 50% NaOH (aqueous) and extract with EtOAc. Dry the extract over $MgSO_4$ and concentrate in vacuo to a residue. Chromatograph the residue (silica gel, 20%–30% EtOAc/hexane) to give 3.47 g of the product (along with another 1.28 g of partially purified product). Mass Spec.: MH$^+$=555.9. $^1$H NMR (CDCl$_3$, 300 MHz): 8.5 (s, 1H); 7.5 (s, 1H); 7.15 (s, 1H); 4.5 (s, 2H); 4.15 (m, 3H); 3.8 (br s, 2H); 3.4–3.1 (m, 4H); 9–2.75 (m, 1H); 2.7–2.5 (m, 2H); 2.4–2.2 (m, 2H); 1.25 (m, 3H).

Step D:

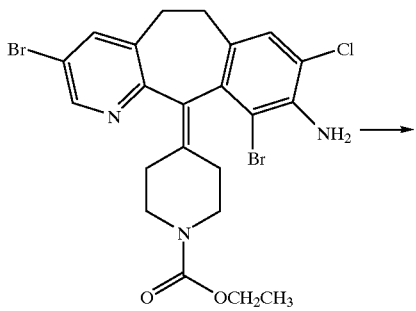

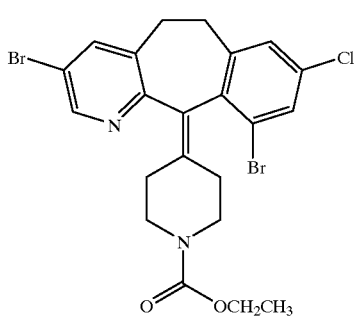

Combine 0.557 g (5.4 mmol) of t-butylnitrite and 3 mL of DMF, and heat the mixture at to 60°–70° C. Slowly add (dropwise) a mixture of 2.00 g (3.6 mmol) of the product of Step C and 4 mL of DMF, then cool the mixture to room temperature. Add another 0.64 mL of t-butylnitrite at 40° C. and reheat the mixture to 60°–70° C. for 0.5 hrs. Cool to room temperature and pour the mixture into 150 mL of water. Extract with $CH_2Cl_2$, dry the extract over $MgSO_4$ and concentrate in vacuo to a residue. Chromatograph the residue (silica gel, 10%–20% EtOAc/hexane) to give 0.74 g of the product. Mass Spec.: $MH^+$=541.0.

$^1$H NMR (CDCl$_3$, 200 MHz): 8.52 (s, 1H); 7.5 (d, 2H); 7.2 (s, 1H); 4.15 (q, 2H); 3.9–3.7 (m, 2H); 3.5–3.1 (m, 4H); 3.0–2.5 (m, 2H); 2.4–2.2 (m, 2H); 2.1–1.9 (m, 2H); 1.26 (t, 3H).

Step E:

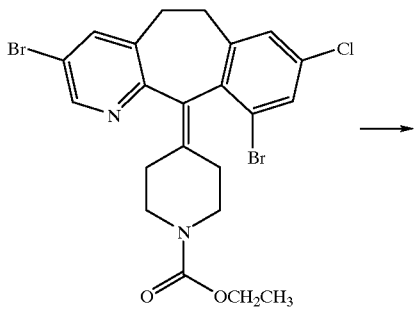

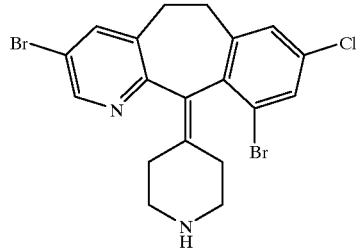

Combine 0.70 g (1.4 mmol) of the product of Step D and 8 mL of concentrated HCl (aqueous) and heat the mixture at reflux overnight. Add 30 mL of 1 N NaOH (aqueous), then 5 mL of 50% NaOH (aqueous) and extract with $CH_2Cl_2$. Dry the extract over $MgSO_4$ and concentrate in vacuo to give 0.59 g of the title compound. Mass Spec.: $M^+$=468.7. m.p.=123.91–124.2° C.

PREPARATION EXAMPLE 6

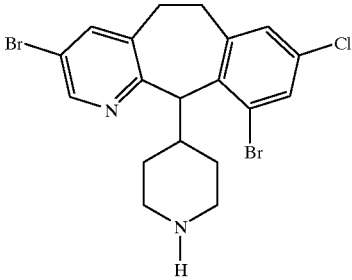

[racemic as well as (+)- and (-)-isomers]

Step A:

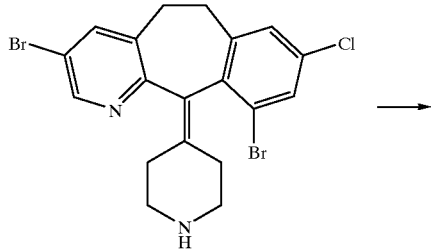

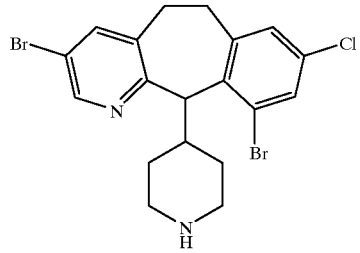

Prepare a solution of 8.1 g of the title compound from Preparative Example 5, Step E, in toluene and add 17.3 mL of a IM solution of DIBAL in toluene. Heat the mixture at reflux and slowly add (dropwise) another 21 mL of 1 M DIBAL/toluene solution over a period of 40 min. Cool the reaction mixture to about 0° C. and add 700 mL of 1 M HCl (aqueous). Separate and discard the organic phase. Wash the aqueous phase with $CH_2Cl_2$, discard the extract, then basify the aqueous phase by adding 50% NaOH (aqueous). Extract with CH$_2$Cl$_2$, dry the extract over MgSO$_4$ and concentrate in vacuo to give 7.30 g of the title compound, which is a racemic mixture of enantiomers.

Step B - Separation of Enantiomers:

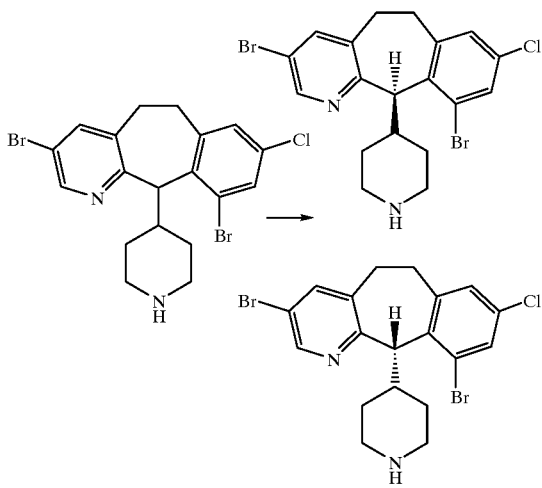

The racemic title compound of Step A is separated by preparative chiral chromatography (Chiralpack AD, 5 cm×50 cm column, using 20% iPrOH/hexane +0.2% diethylamine), to give the (+)-isomer and the (−)-isomer of the title compound.

Physical chemical data for (+)-isomer: m.p.=148.8° C.; Mass Spec. MH$^+$=469; [α]=+65.6° (12.93 mg/2 mL MeOH).

Physical chemical data for (−)-isomer: m.p.=112° C.; Mass Spec. MH$^+$=469; [α]=−65.2° (3.65 mg/2 mL MeOH).

PREPARATION EXAMPLE 7

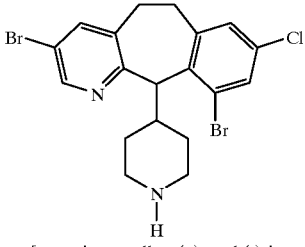

[racemic as well as (+)- and (−)-isomers]

Step A:

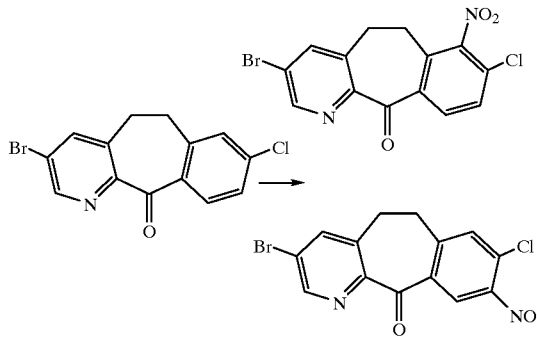

Combine 40.0 g (0.124 mole) of the starting ketone and 200 mL of H$_2$SO$_4$ and cool to 0° C. Slowly add 13.78 g (0.136 mole) of KNO$_3$ over a period of 1.5 hrs., then warm to room temperature and stir overnight. Work up the reaction using substantially the same procedure as described for Preparative Example 2, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds.

Step B:

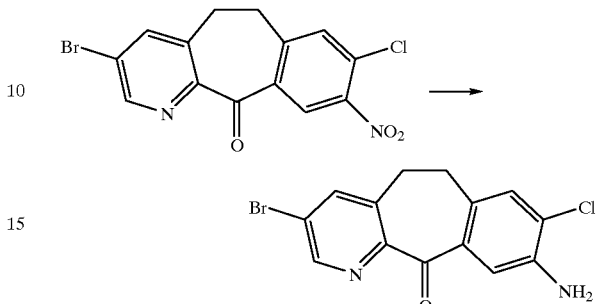

React 28 g (76.2 mmol) of the 9-nitro product of Step A, 400 mL of 85% EtOH/water, 3.8 g (34.3 mmol) of CaCl$_2$ and 38.28 g (0.685 mole) of Fe using substantially the same procedure as described for Preparative Example 2, Step C, to give 24 g of the product Step C:

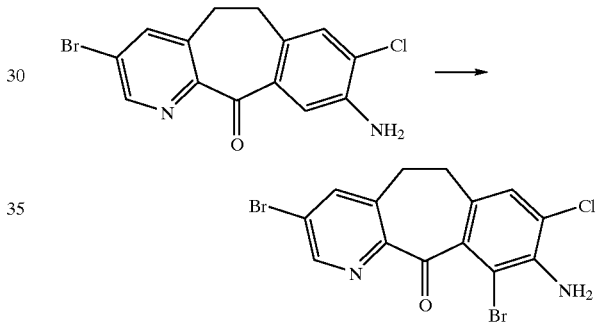

Combine 13 g (38.5 mmol) of the product of Step B, 140 mL of HOAc and slowly add a solution of 2.95 mL (57.8 mmol) of Br$_2$ in 10 mL of HOAc over a period of 20 min. Stir the reaction mixture at room temperature, then concentrate in vacuo to a residue. Add CH$_2$Cl$_2$ and water, then adjust to pH=8–9 with 50% NaOH (aqueous). Wash the organic phase with water, then brine and dry over Na$_2$SO$_4$. Concentrate in vacuo to give 11.3 g of the product.

Step D:

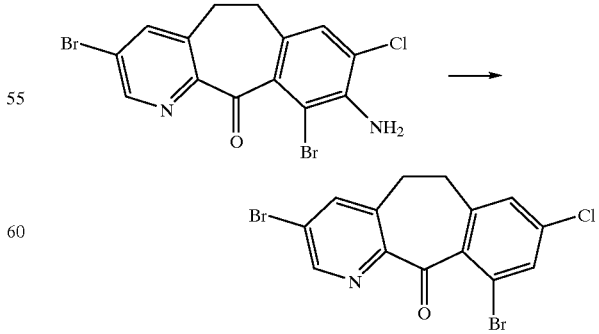

Cool 100 mL of concentrated HCl (aqueous) to 0° C., then add 5.61 g (81.4 mmol) of NaNO$_2$ and stir for 10 min.

Slowly add (in portions) 11.3 g (27.1 mmol) of the product of Step C and stir the mixture at 0°–3° C. for 2.25 hrs. Slowly add (dropwise) 180 mL of 50% $H_3PO_2$ (aqueous) and allow the mixture to stand at 0° C. overnight. Slowly add (dropwise) 150 mL of 50% NaOH over 30 min., to adjust to pH=9, then extract with $CH_2Cl_2$. Wash the extract with water, then brine and dry over $Na_2SO_4$. Concentrate in vacuo to a residue and chromatograph (silica gel, 2% EtOAc/$CH_2Cl_2$) to give 8.6 g of the product.

Step E:

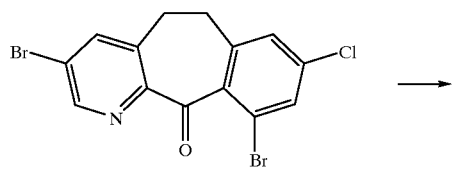

Combine 8.6 g (21.4 mmol) of the product of Step D and 300 mL of MeOH and cool to 0°–2° C. Add 1.21 g (32.1 mmol) of $NaBH_4$ and stir the mixture at ~0° C. for 1 hr. Add another 0.121 g (3.21 mmol) of $NaBH_4$, stir for 2 hr. at 0° C., then let stand overnight at 0° C. Concentrate in vacuo to a residue then partition the residue between $CH_2Cl_2$ and water. Separate the organic phase and concentrate in vacuo (50° C.) to give 8.2 g of the product.

Step F:

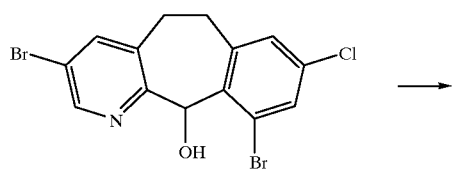

Combine 8.2 g (20.3 mmol) of the product of Step E and 160 mL of $CH_2Cl_2$, cool to 0° C., then slowly add (dropwise) 14.8 mL (203 mmol) of $SOCl_2$ over a 30 min. period. Warm the mixture to room temperature and stir for 4.5 hrs., then concentrate in vacuo to a residue, add $CH_2Cl_2$ and wash with 1 N NaOH (aqueous) then brine and dry over $Na_2SO_4$. Concentrate in vacuo to a residue, then add dry THF and 8.7 g (101 mmol) of piperazine and stir at room temperature overnight. Concentrate in vacuo to a residue, add $CH_2Cl_2$, and wash with 0.25 N NaOH (aqueous), water, then brine. Dry over $Na_2SO_4$ and concentrate in vacuo to give 9.46 g of the crude product. Chromatograph (silica gel, 5% MeOH/$CH_2Cl_2$+$NH_3$) to give 3.59 g of the title compound, as a racemate. $^1H$ NMR ($CDCl_3$, 200 MHz): 8.43 (d, 1H); 7.55 (d, 1H); 7.45 (d, 1H); 7.11 (d, 1H); 5.31 (s, 1H); 4.86–4.65 (m, 1H); 3.57–3.40 (m, 1H); 2.98–2.55 (m, 6H); 2.45–2.20 (m, 5H).

Step G -Separation of Enantiomers:

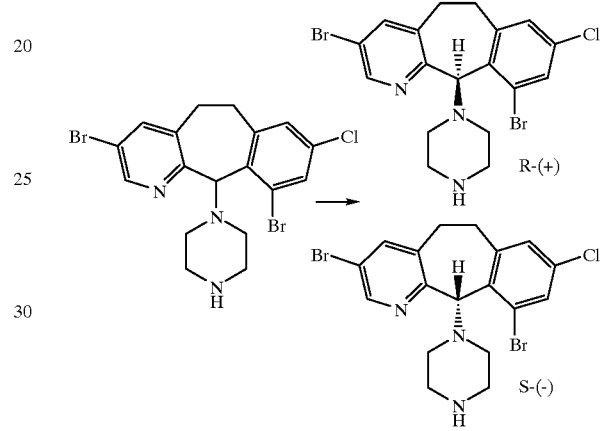

The racemic title compound from Step F (5.7 g) is chromatographed as described for Preparative Example 4, Step D, using 30% iPrOH/hexane+0.2% diethylamine, to give 2.88 g of the R-(+)-isomer and 2.77 g of the S-(−)-isomer of the title compound.

Physical chemical data for the R-(+)-isomer: Mass Spec. $MH^+$=470.0; [α]=+12.1° (10.9 mg/2 mL MeOH).

Physical chemical data for the S-(−)-isomer: Mass Spec. $MH^+$=470.0; [α]=−13.2° (11.51 mg/2 mL MeOH).

PREPARATIVE EXAMPLE 8

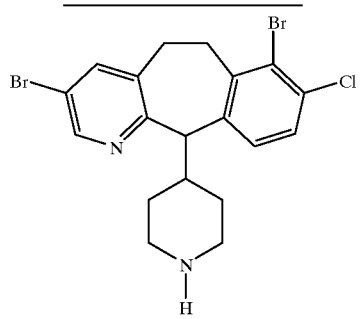

[racemic as well as (+)- and (−)-isomers]

Step A:

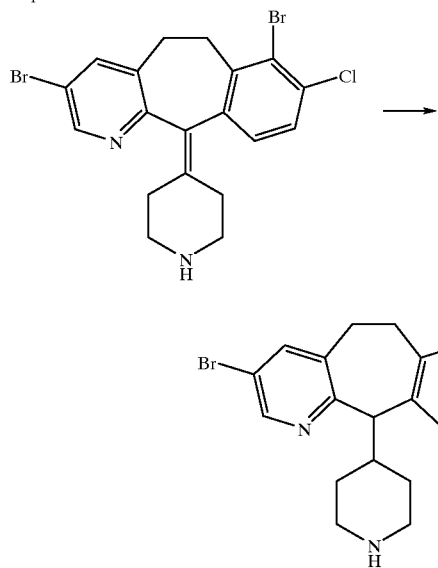

Combine 13 g (33.3 mmol) of the title compound from Preparative Example 2, Step E, and 300 mL of toluene at 20° C., then add 32.5 mL (32.5 mmol) of a 1 M solution of DIBAL in toluene. Heat the mixture at reflux for 1 hr., cool to 20° C., add another 32.5 mL of 1 M DIBAL solution and heat at reflux for 1 hr. Cool the mixture to 20° C. and pour it into a mixture of 400 g of ice, 500 mL of EtOAc and 300 mL of 10% NaOH (aqueous). Extract the aqueous layer with $CH_2Cl_2$ (3×200 mL), dry the organic layers over $MgSO_4$, then concentrate in vacuo to a residue. Chromatograph (silica gel, 12% $MeOH/CH_2Cl_2$+4% $NH_4OH$) to give 10.4 g of the title compound as a racemate. Mass Spec.: $MH^+$=469 (FAB). Partial $^1H$ NMR ($CDCl_3$, 400 MHz): 8.38 (s, 1H); 7.57 (s, 1H); 7.27 (d, 1H); 7.06 (d, 1H); 3.95 (d, 1H).

Step B - Separation of Enantiomers:

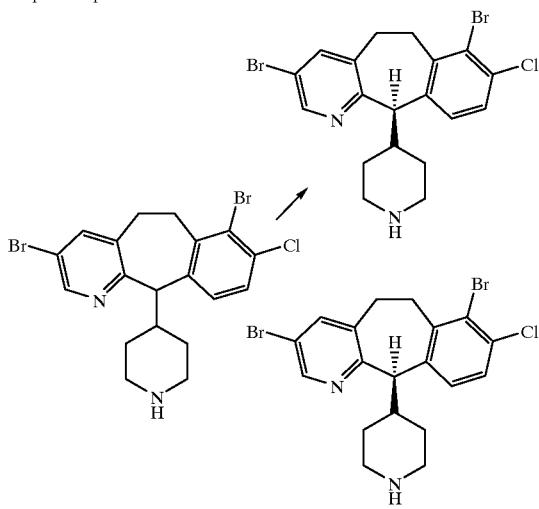

The racemic title compound of Step A is separated by preparative chiral chromatography (Chiralpack AD, 5 cm×50 cm column, using 5% iPrOH/hexane+0.2% diethylamine), to give the (+)-isomer and the (−)-isomer of the title compound.

Physical chemical data for (+)-isomer: Mass Spec. $MH^+$=469 (FAB); [α]=+43.5° (c=0.402, EtOH); partial $^1H$ NMR ($CDCl_3$, 400 MHz): 8.38 (s, 1H); 7.57 (s, 1H); 7.27 (d, 1H); 7.05 (d, 1H); 3.95 (d, 1H).

Physical chemical data for (−)-isomer: Mass Spec. $MH^+$=469 (FAB); [α]=−41.8° (c=0.328 EtOH); partial $^1H$ NMR ($CDCl_3$, 400 MHz): 8.38 (s, 1H); 7.57 (s, 1H); 7.27 (d, 1H); 7.05 (d, 1H); 3.95 (d, 1H).

PREPARATIVE EXAMPLE 9

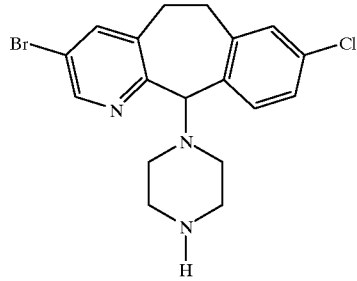

[racemic as well as R-(+)- and S-(−)-isomers]

The compound

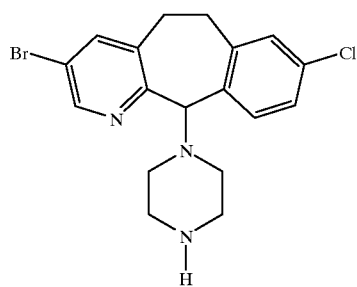

is prepared according to the procedures of Preparative Example 40 of WO 95/10516 (published Apr. 20, 1995), by following the procedures described in Example 193 of WO 95/10516.

The (+)- and (−)-isomers can be separated by following essentially the same procedure as Step D of Preparative Example 4.

Physical chemical data for the R-(+)-isomer: $^{13}C$ NMR ($CDCl_3$): 155.8 (C); 146.4 (CH); 140.5 (CH); 140.2 (C); 136.2 (C); 135.3 (C); 133.4 (C); 132.0 (CH); 129.9 (CH); 125.6 (CH); 119.3 (C); 79.1 (CH); 52.3 ($CH_2$); 52.3 (CH); 45.6 ($CH_2$); 45.6 ($CH_2$); 30.0 ($CH_2$); 29.8 ($CH_2$). [α]=+25.8° (8.46 mg/2 mL MeOH).

Physical chemical data for the S-(−)-isomer: $^{13}C$ NMR ($CDCl_3$): 155.9 (C); 146.4 (CH); 140.5 (CH); 140.2 (C); 136.2 (C); 135.3 (C); 133.3 (C); 132.0 (CH); 129.9 (CH); 125.5 (CH); 119.2 (C); 79.1 (CH); 52.5 ($CH_2$); 52.5 (CH); 45.7 ($CH_2$); 45.7 ($CH_2$); 30.0 ($CH_2$); 29.8 ($CH_2$). [α]=−27.9° (8.90 mg/2 mL MeOH).

PREPARATIVE EXAMPLE 10

Step A:

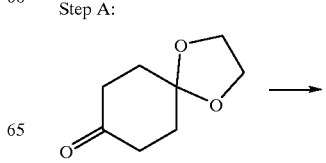

-continued

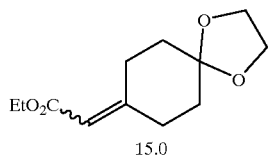
15.0

A solution of 1,4-cyclohexandione monoketal (3.00 g, 19.21 mmol) and Ph$_3$P=CH$_2$CO$_2$Et (7.36 g, 21.13 mmol) in toluene (60 mL) was heated to reflux 3 days. The reaction mixture was cooled, concentrated in vacuo and the residue diluted with Et$_2$O. The resulting slurry was filtered and the Et$_2$O removed in vacuo and the product purified by flash chromatography (30% EtOAc in hexane) to give compound 15.0 as a clear oil (79% yield).

Step B:

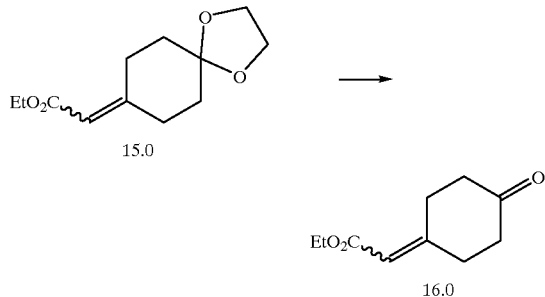

A solution of compound 15.0 from Preparative Example 10A (3.43 g, 16.16 mmol) and 1N H$_2$SO$_4$ (3 mL) in acetone (150 mL) was stirred at room temperature 3 days. The reaction mixture was poured into saturated NaHCO$_3$ (150 mL) and extracted with CH$_2$Cl$_2$ (3×75 mL). The combined organics were washed with water (1×50 mL), dried over Na$_2$SO$_4$, and concentrated in vacuo to give compound 16.0 as a pale yellow oil (2.90 g, 100% crude yield).

Step C:

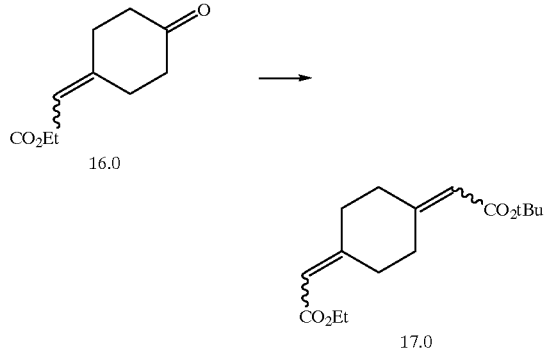

By essentially the same procedure as described in Preparative Example 10A, compound 16.0 from Preparative Example 10B (2.00 g, 10.98 mmol) and Ph$_3$P=CHCO$_2$tBu (4.55 g, 12.08 mmol) was heated to reflux in toluene (50 mL). The crude product was purified by flash chromatography (10% EtOAc in hexanes) to give compound 17.0 as a clear oil (2.12 g, 69% yield).

Step D:

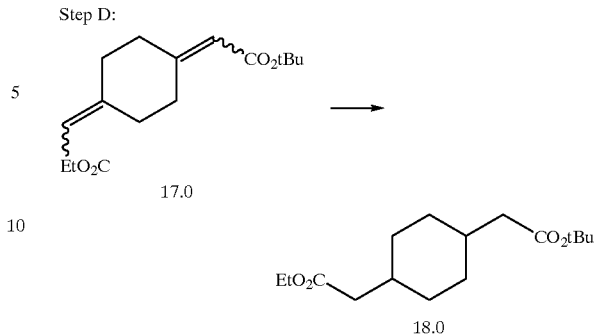

A solution of compound 17.0 from Preparative Example 10C (0.75 g, 2.68 mmol) and 10% Pd/C (0.72 g) in ethyl acetate (8 mL) was hydrogenated (balloon pressure) for 14 hours. The resulting solution was filtered through a plug of Celite and concentrated in vacuo to give compound 18.0 as a clear oil (0.70 g, 92% crude yield).

Step E:

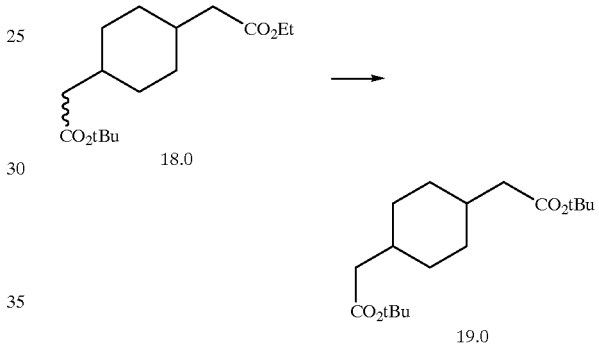

A solution of compound 18.0 from Preparative Example 10D (0.29 g, 1.02 mmol) and K$_2$CO$_3$ (0.35 g, 2.55 mmol) in 2:1 MeOH H$_2$O was heated at reflux 5 hours. The resulting solution was cooled, concentrated, diluted with H$_2$O (25 mL) and washed with Et$_2$O. The aqueous layer was acidified with 1N HCl and extracted with EtOAc (3×25 mL). The combined organics were dried over Na$_2$SO$_4$, and concentrated in vacuo to give compound 19.0 as a white solid (0.25 g, 97% yield).

PREPARETION EXAMPLE 11

Step A:

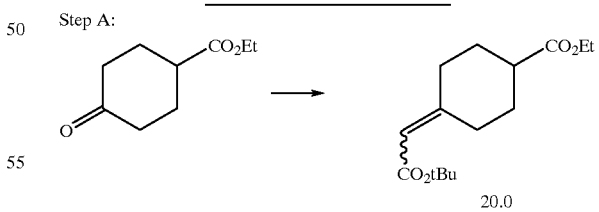

A solution of ethyl 4-oxocyclohexane carboxylate (5.00 g, 29.38 mmol) and Ph$_3$P=CH$_2$CO$_2$tBu (12.16 g, 35.26 mmol) in toluene (150 mL) was heated to reflux 24 hours. The resulting solution was cooled, concentrated, and diluted with a 70:30 Et$_2$O hexane solution. The resulting slurry was filtered and the filtrate concentrated in vacuo. The crude product was purified by flash chromatography (5% EtOAc in hexanes) to give compound 20.0 as a clear oil (3.90 g, 49% yield).

Step B:

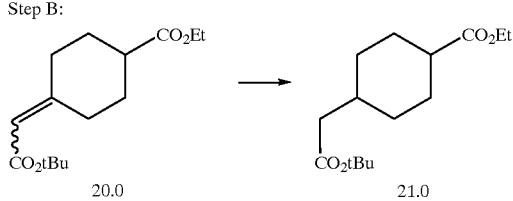

By essentially the same procedure described in Preparative Example 10D, a solution of compound 20.0 from Preparative Example 11A (3.90 g, 14.53 mmol) and 10% Pd/C (1.95 g) was hydrogenated to give Compound 21.0 as a clear oil (3.85 g, 98% yield).

Step C:

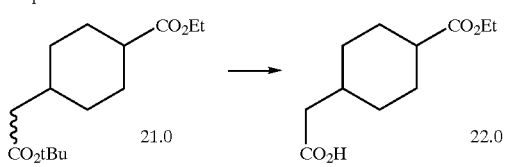

A solution of compound 21.0 from Preparative Example 11B (0.25 g, 0.93 mmol) in $CH_2Cl_2$ (0.5 mL) was treated with trifluoroacetic acid (0.5 mL) and stirred at room temperature 5 hours. The resulting solution was concentrated, taken up $Et_2O$ and extracted with 1N NaOH (2×15 mL). The aqueous layers were combined, extracted with $Et_2O$ (1×10 mL), neutralized with 1N HCl and extracted with EtOAc (3×20 mL). The combined organics were dried over $Na_2SO_4$ and concentrated in vacuo to give compound 22.0 as a white solid (0.19 g, 96% yield).

PREPARATIVE EXAMPLE 12

Step A:

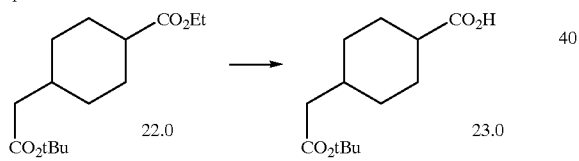

By essentially the same procedure described in Preparative Example 10E, a solution of compound 22.0 from Preparative Example 11B (3.80 g, 14.05 mmol) was treated with $K_2CO_3$ (4.85 g, 35.12 mmol) to give compound 23.0 as a white solid (3.30 g, 97% yield).

PREPARATIVE EXAMPLE 13

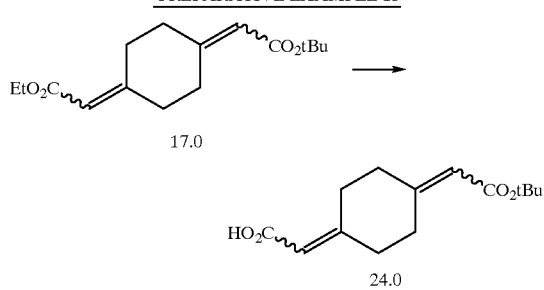

Compound 17.0 from Preparative Example 10C (0.25 g, 0.89 mmol) and $K_2CO_3$ (0.31 g, 2.23 mmol) was heated to reflux in MeOH:$H_2O$ to give compound 24.0 (0.15 g, 68% yield).

PREPARATIVE EXAMPLE 14

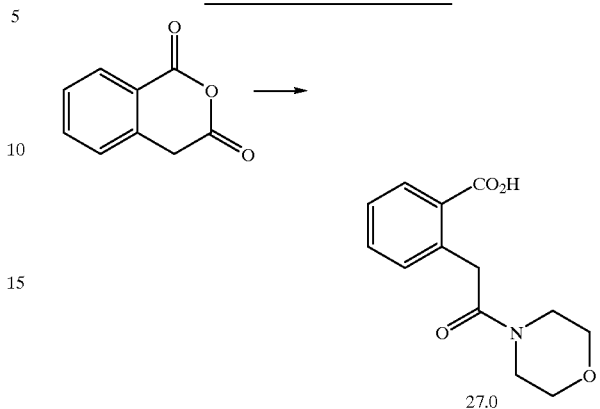

Compound 27.0 was prepared using basically the same procedure as described in Example 1 by substituting morpholine (0.065 g) and homophthalic anhydride (0.10 g, 0.617 mmol) in THF (2 mL) (0.11 g, 73% yield).

EXAMPLE 1

Step A:

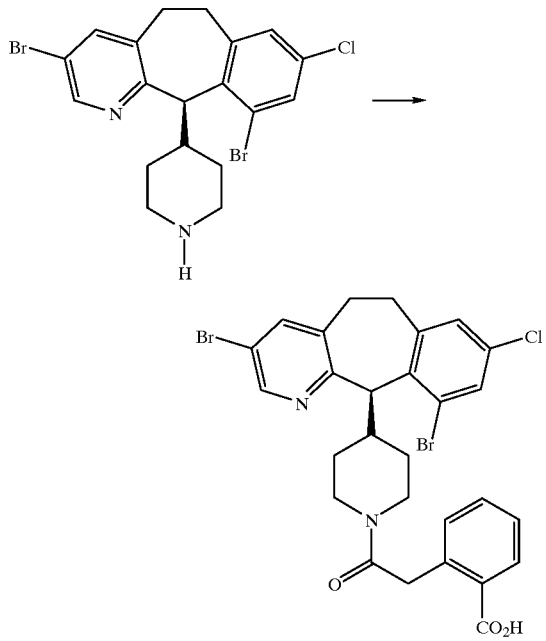

A solution of amine from Preparative Example 6 0.35 g, 0.744 mmol) and homophthalic anhydride (0.15 g, 0.89 mmol) in THF (5 mL) was stirred at room temperature 36 hours. The resulting solution was diluted with EtOAc (15 mL), washed with 50% NaOH (10 mL) and $H_2O_2$. The aqueous layer was acidified with 1N HCl and extracted with EtOAc (3×15 mL), dried over $Na_2SO_4$, and concentrated to yield compound 25.0 (0.3 g, 65% yield, mp=229° C. (dec.).

By essentially the procedure of Example 1, but using the carboxylic acid anhydride in Column 1, one can obtain compounds of the formula shown below wherein R is as listed in Column 2 of Table 1.

TABLE 1

| Ex. | Column 1 | Column 2 | CMPD |
|---|---|---|---|
| 2 | 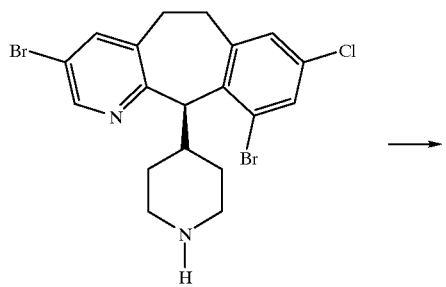 | | white solid mp = 192–194° C. |

EXAMPLE 3

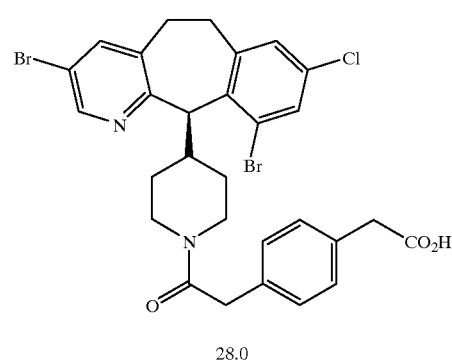

A solution of amine (0.75 g, 1.59 mmol) from Preparative Example, 1,4-phenylene diacetic acid (093 g, 4.77 mmol), 1-hydroxybenzotriazole (0.54 g, 3.98 mmol), 1-(3-Dimethylaminopropyl)-3-ethylcarbodiimide HCl (0.76 g, 3.98 mmol), and N-methylmorpholine (0.87 mL, 7.95 mmol) in $CH_2Cl_2$ (15 mL) was stirred 18 hours. The solution was diluted with 1N HCl (50 mL) and $CH_2Cl_2$ (25 mL), separated, and the organic layer concetrated in vacou. The residue was taken up in saturated $NaHCO_3$ (50 mL), washed with EtOAc (50 mL), acidified with 1N HCl, and extracted with EtoAC (3×30 mL). The combined organics were dried over $Na_2SO_4$, concentrated in vacuo, and the crude product purified by flash chromatography (92:5:3 $CH_2Cl_2$:MeOH:AcOH) to give compound 28.0 (0.5 g, 49% yield) mp=186–189° C.

By essentially the same procedure as Example 3, but using the carboxylic acid in Column 1, one can obtain compounds of the formula shown below wherein R is as listed in Column 2 of Table 2.

TABLE 2

| Ex. | Column 1 | Column 2 | CMPD |
|---|---|---|---|
| 4 | | | 29.0 white solid mp = 205° C. (dec.) |
| 5 | | | 30.0 white solid mp = 138–140° C. |

EXAMPLE 6

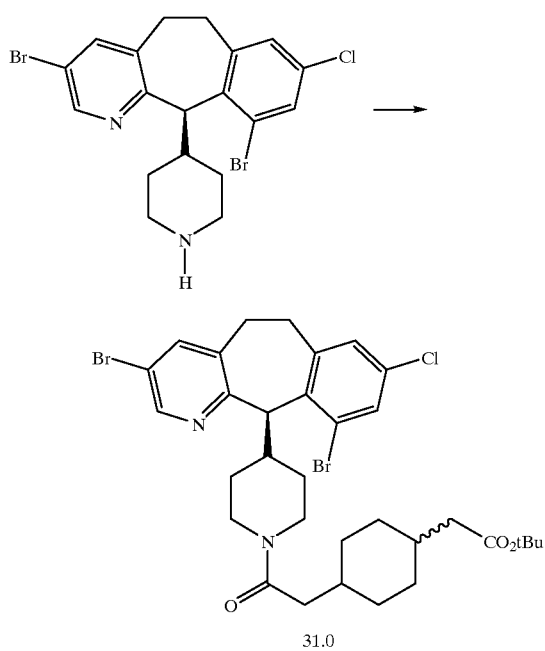

A solution of amine (0.38 g, 0.81 mmol) (from Preparative Example 6) compound 19.0 from Preparative Example 10E (0.25 g, 0.97 mmol), 1-hydroxybenzotriazole (0.14 g, 0.97 mmol), 1-(3-dimethylaminopropyl)-3-ethylcarbodiimide HCl (0.20 g, 0.97 mmol), and N-methylmorpholine (0.27 mL, 2.43 mmol) in $CH_2Cl_2$ (5 mL) was stirred 36 hours. The solution was diluted with $H_2O$ (25 mL), separated and the aqueous layer extracted with $CH_2Cl_2$ (2×15 mL). The combined organics were dried over $Na_2SO_4$, concentrated in vacuo, and the crude product purified by flash chromatography (10% hexanes in EtOAc) to give compound 31.0 (0.49 g, 87% yield) mp=86–90 C By essentially the same procedure, but using the carboxylic acid given in Column 1, one can obtain compounds of the formula shown below wherein R is as listed in Column 2 of Table 3.

TABLE 3

| Ex. | Column 1 | Column 2 | CMPD |
|---|---|---|---|
| 7 | OH-...-CO2tBu | ...-CO2tBu  32.0 | white solid  mp = 113–117° C. |
| 8 | OH-...-CO2Et | ...-CO2Et  33.0 | white solid  mp = 88–94° C. |

TABLE 3-continued
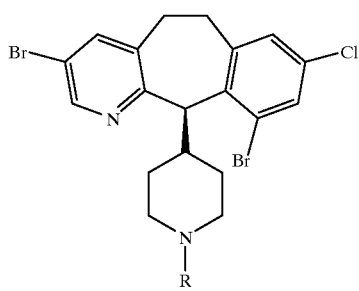
| Ex. | Column 1 | Column 2 | CMPD |
|---|---|---|---|
| 9 | (structure with OH, CO₂H, CO₂tBu) | (structure with wavy bond, C=O, CO₂tBu) 34.0 | white solid mp = 98–102° C. |
| 10 | (structure with OH, CO₂H, CO₂tBu) | (structure with wavy bond, C=O, CO₂tBu) 35.0 | white solid mp = 98–102° C. |
| 11 | (benzoic acid with morpholine amide) | (ketone with morpholine amide) | white solid mp = 127–128° C. |
EXAMPLE 12
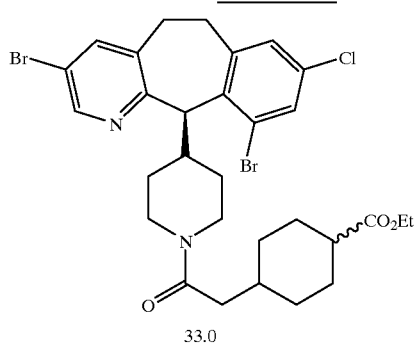
33.0
→
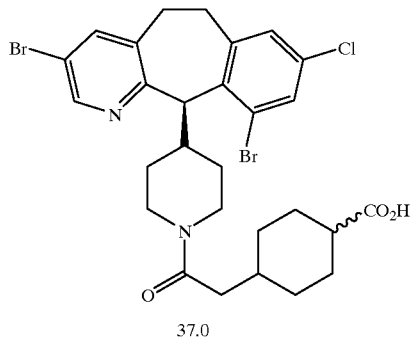
37.0

By using essentially the same procedure as set forth in Preparative Example 10E, the title compound was prepared from compound 33.0 from Example 8 (85% yield) mp=146–150° C.

EXAMPLE 13

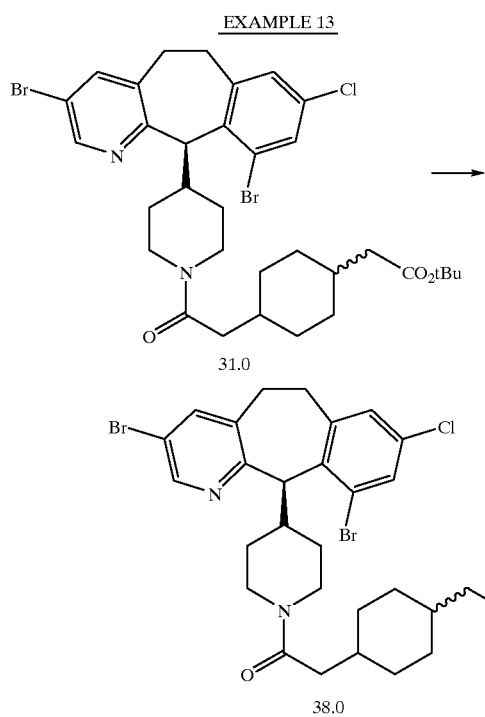

By essentially the same procedure set forth in Preparative Example 11C, compound 38.0 was prepared from compound 31.0 of Example 6 (50% yield) mp=178–183° C.

EXAMPLE 14

By essentially the same procedure as in Example 14, but using the compound shown in Column 1, one can obtain compounds of the formula shown below wherein R is as listed in Column 2 of Table 4.

EXAMPLE 15

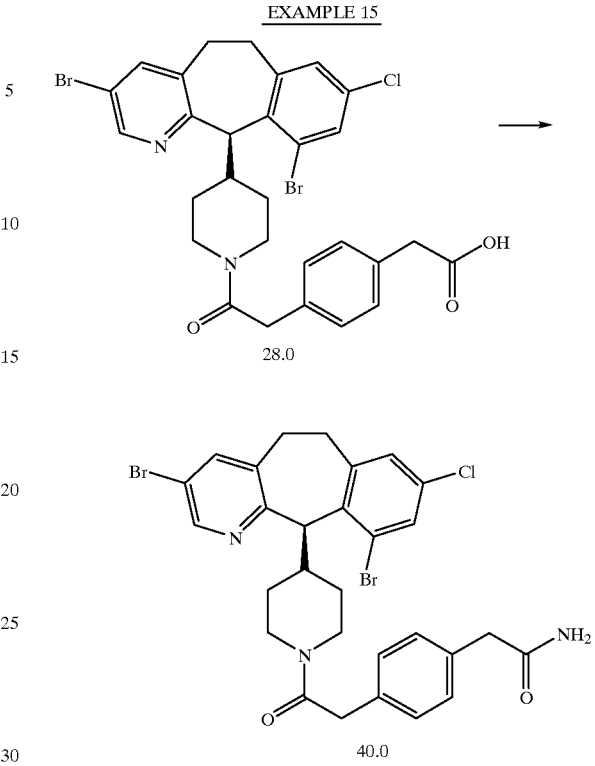

By essentially the same procedure set forth in Example 6, but using compound 28.0 from Example 3 (0.063 g, 0.097 mmol) and $HN_4Cl$, compound 40.0 was prepared (52% yield) mp=135–138° C.

EXAMPLE 16

By essentially the same procedure, but using the amine given in Column 1 with the carboxylic acid in Column 1, one can obtain compounds of the formula shown below wherein R is as listed in Column 2 of Table 5.

TABLE 4

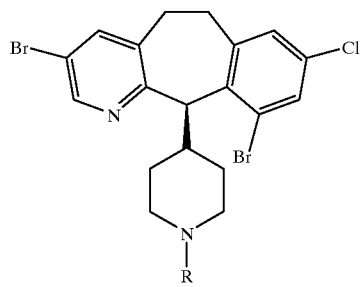

| Ex. | Column 1 | Column 2 | CMPD |
|---|---|---|---|
| 14 | 32.0 (CO₂tBu structure) | 39.0 (CO₂H structure) | white solid mp = 161–169° C. |

TABLE 5
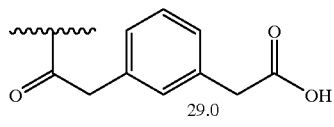
| Ex. | Column 1 | Column 2 | CMPD |
|---|---|---|---|
| 16 | NH₄Cl; 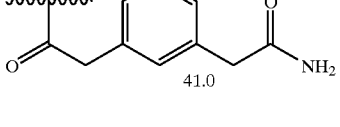 29.0 | 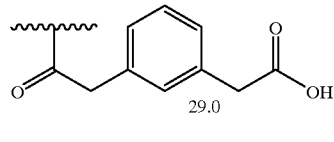 41.0 | white solid mp = 119–125° C. |
| 17 | H₂N-CO₂Me; 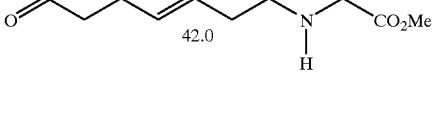 29.0 | 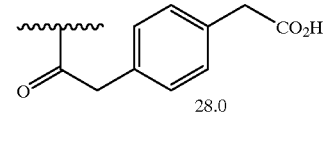 42.0 | white solid mp = 86–90° C. |
| 18 | H₂N-CO₂Me; 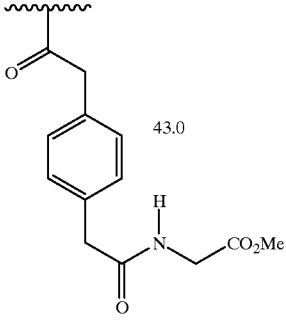 28.0 | 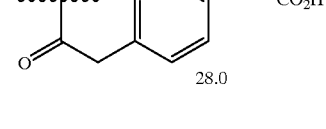 43.0 | white solid mp = 94–97° C. |
| 19 | MeONH₂; 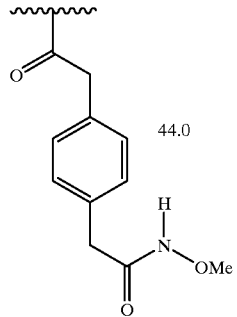 28.0 | 44.0 | white solid mp = 116–123° C. |

TABLE 5-continued
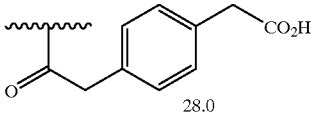
| Ex. | Column 1 | Column 2 | CMPD |
|---|---|---|---|
| 20 | 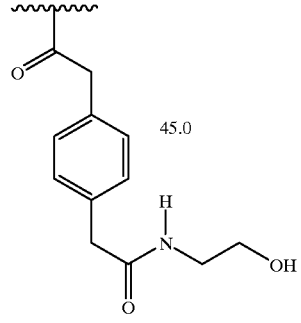 | 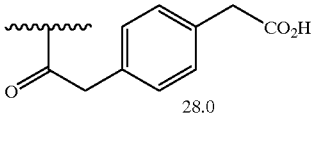 | white solid mp = 94–100° C. |
| 21 | 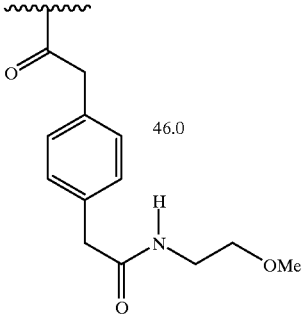 | 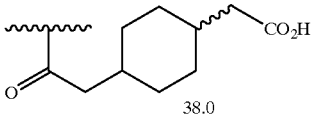 | white solid mp = 97–102° C. |
| 22 | NH₄Cl; 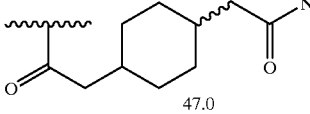 | 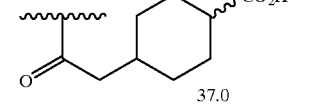 | white solid mp = 103–110° C. |
| 23 | NH₄Cl; 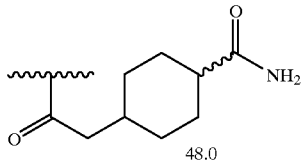 | 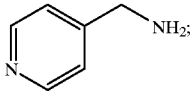 | white solid mp = 145–152° C. |
| 24 | 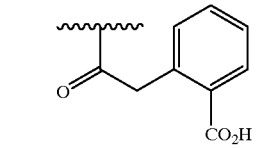 | 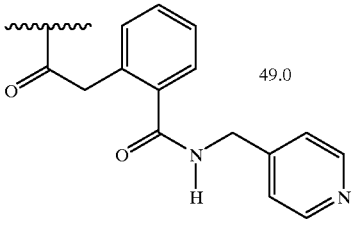 | white solid mp = 134–138° C. |

TABLE 5-continued
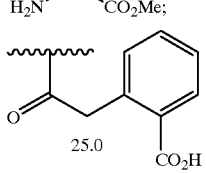
| Ex. | Column 1 | Column 2 | CMPD |
|---|---|---|---|
| 25 | 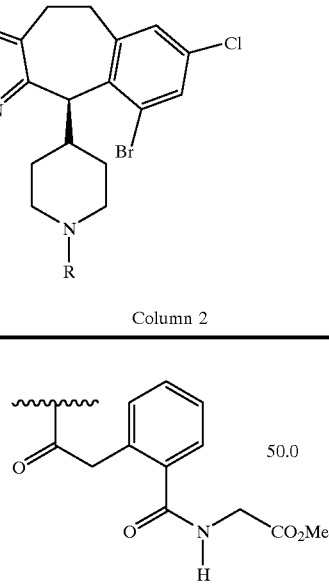 H₂N―CO₂Me; 25.0 | 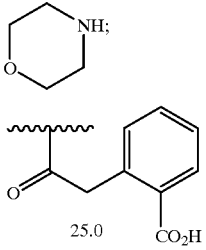 50.0 | white solid mp = 116–118° C. |
| 26 | 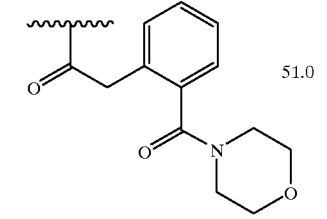 morpholine NH; 25.0 | 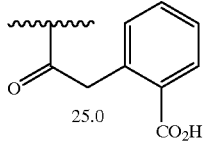 51.0 | white solid mp = 136–138° C. |
| 27 | 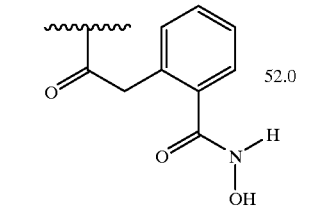 HONH₂; 25.0 | 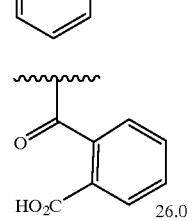 52.0 | white solid mp = 156–157° C. |
| 28 | 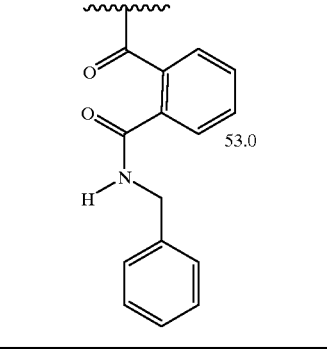 PhCH₂NH₂; 26.0 | (benzylamide) 53.0 | white solid mp = 117–119° C. |

EXAMPLE 29

Trans-2(R)-[[4-(3,10-dibromo-8-chloro-6,11-dihydro-5H-benzo[5,6]cyclohepta[1,2-b]pyridin-11(R)-yl)-1-piperidinyl]carbonyl]-(R)-cyclopropanecarboxamide

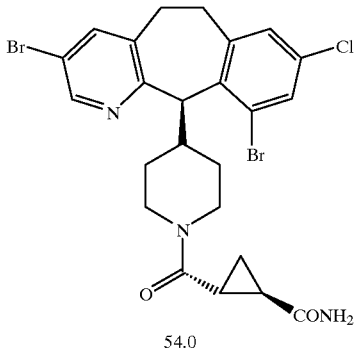

54.0

Step 1: Trans-methyl 2(R)-[[4-(3,10-dibromo-8-chloro-6,11-dihydro-5H-benzo[5,6]cyclopenta[1,2-b]pyridin-11(R)-yl)-1-piperidinyl]carbonyl]-(R) cyclopropanecarboxylate

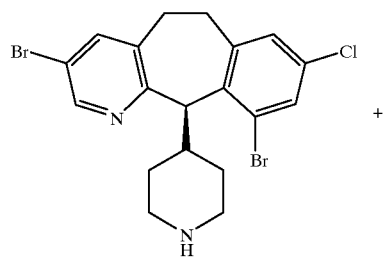

+

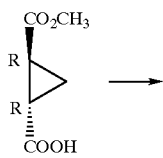

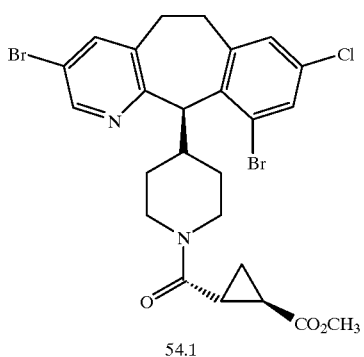

54.1

Dissolve 1.0 g (2.34 mmol) of the amine (from Preparative Example 6) in 20 ml of DMF, stir at room temperature, and add 0.77 g (7.5 mmol) of 4-methylmorpholine, 0.44 g (2.29 mmol) of 20 DEC, 0.0.31 g (2.29 mmol) of HOBT, and 0.33 g (2.28 mmole)of R)-(−) trans-2(R) methoxycarbonylcyclopropyl-1(R)carboxylic acid ((Prepared according to the lit. Organic Synthesis 67,76, 1988) Stir the mixture at room temperature for 2 days, then concentrate in vacuo to a residue, then partition the residue between $CH_2Cl_2$ and water. Wash the organic phase successively with saturated $NaHCO_3$ (aqueous), and brine. Dry the organic phase over $MgSO_4$ and concentrate in in vacuo to a residue. Chromatograph the residue (silica gel, Hexane-25% ethyl acetate) to give 1.05 g of the title comound(54.1) Mass Spec.: $MH^+$596 partial $^1H$ NMR ($CDCl_3$, 200 MHz): 8.42 (d, 1H); 7.54 (bs, 1H); 7.50 (bs, 1H); 7.12 (s, 1H); 4.90(d, 1H); 4.55 (d, 1H), 3.7 (s, 3H).

Step 2:

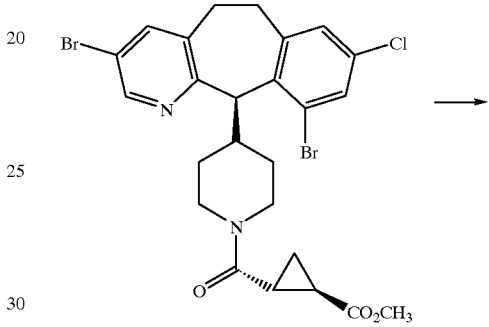

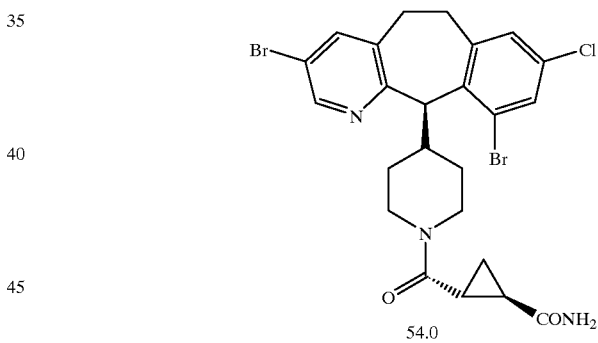

54.0

Dissolve 0.91 g (1.52 mmol) of the compound from Step 1 in methanol (10 ml) and add 1N NaOH (2.27 ml, 2.27 mmol) and stirr overnight at 80° C. Evaporate to dryness. Dissolve the residue in DMF and add 0.77 g (7.5 mmol) of 4-methylmorpholine, 0.44 g (2.29 mmol) of DEC, 0.0.31 g (2.29 mmol) of HOBT, and 0.16 g (2.99 mmol) of ammonium chloride Stir the mixture at room temperature overnight, then concentrate in vacuo to a residue, then partition the residue between $CH_2Cl_2$ and water. Wash the organic phase successively with brine. Dry the organic phase over $MgSO_4$ and concentrate in in vacuo to a residue. Chromatograph the residue (silica gel, $CH_2Cl_2$/5% ($CH_3OH$-10% $NH_4OH$)) to give 0.72 g of the title comound (54.0) Mass Spec.: $MH^+$581 partial $^1H$ NMR ($CDCl_3$, 400 MHz): 8.42 (s, 1H); 7.54 (d, 1H); 7.52 (d, 1H); 7.12 (s, 1H); 6.05 (d, 1H), 5.5 (d, 1H).

EXAMPLE 30

Trans-2(S)-[[4-(3,10-dibromo-8-chloro-6,11-dihydro-5H-benzo[5,6]cyclohepta[1,2-b]pyridin-11(R)-yl)-1-piperidinyl]carbonyl]-(S)-cyclopropanecarboxamide

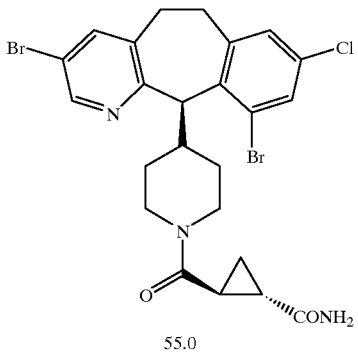

55.0

Step 1: Trans-methyl 2(S)-[[4-(3,10-dibromo-8-chloro-6,11-dihydro-5H-benzo[5,6]cyclohepta[1,2-b]pyridin-11(R)-yl)-1-piperidinyl]carbonyl]-(S) cyclopropanecarboxylate

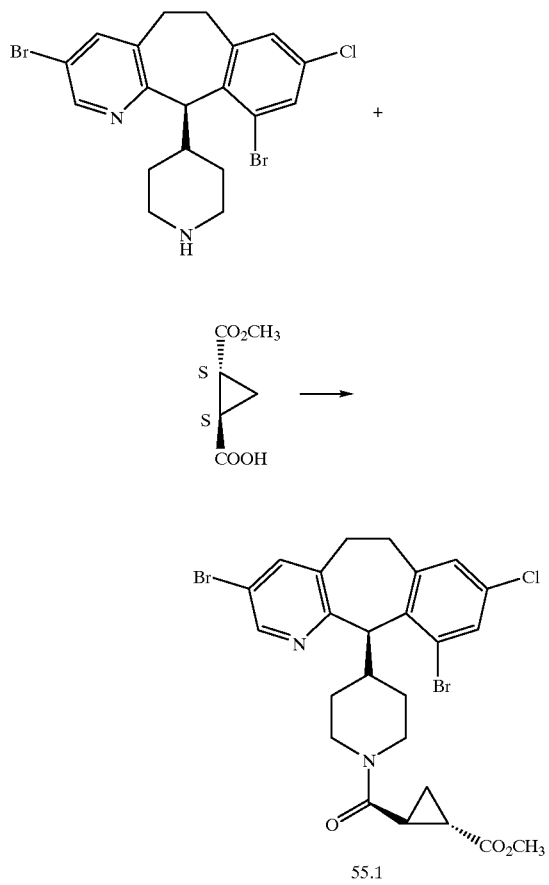

55.1

Dissolve 0.5 g (0.52 mmol) of the amine (from Preparative Example 6) in 10 ml of DMF, stir at room temperature, and add 0.156 g (1.53 mmol) of 4-methylmorpholine, 0.148 g (0.77 mmol) of DEC, 0.0.104 g (0.77 mmol) of HOBT, and 0.12 g (0.77 mmole) of R)-(−) trans-2(S) methoxycarbonylcyclopropyl-1(S)carboxylic acid (Prepared according to the lit. Organic Synthesis 67,76, 1988) Stir the mixture at room temperature for 2 days, then concentrate in vacuo to a residue, then partition the residue between $CH_2Cl_2$ and water. Wash the organic phase successively with saturated $NaHCO_3$ (aqueous), and brine. Dry the organic phase over $MgSO_4$ and concentrate in in vacuo to a residue. Chromatograph the residue (silica gel, Hexane-25% ethyl acetate) to give 0.582 g of the title comound(55.1). Mass Spec.: $MH^+596$ partial $^1H$ NMR ($CDCl_3$, 400 MHz): 8.45 (S, 1H); 7.54 (bs, 1H); 7.50 (bs, 1H); 7.12 (s, 1H); 4.82(m, 1H); 4.55 (d, 1H), 3.65 (s, 3H).

Step 2:

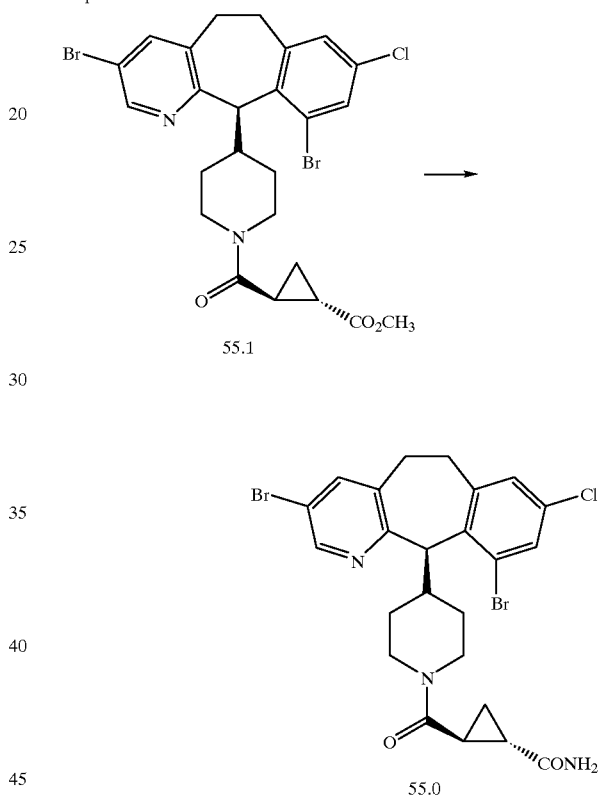

Dissolve 0.472 g (0.77 mmol) of the compound (55.1) in methanol (10 ml) and add 1N NaOH 0.93 ml, 0.92 mmol) and stirr overnight at 80° C. Evaporate to dryness. Dissolve the residue in DMF and add 0.0.392 g (3.86 mmol) of 4-methylmorpholine, 0.0.22 g (1.14 mmol) of DEC, 0.0.0.156 g (1.15 mmol) of HOBT, and 0.0.062 g (1.15 mmol) of ammonium chloride Stir the mixture at room temperature overnight, then concentrate in vacuo to a residue, then partition the residue between $CH_2Cl_2$ and water. Wash the organic phase successively with brine. Dry the organic phase over $MgSO_4$ and concentrate in in vacuo to a residue. Chromatograph the residue (silica gel, $CH_2Cl_2$/5% ($CH_3OH$-10% $NH_4OH$)) to give 0.0.114 g of the title comound(55.0). Mass Spec.: $MH^+581$ partial $^1H$ NMR ($CDCl_3$, 400 MHz): 8.50 (s, 1H); 7.6.0 (bs, 1H); 7.52 (bs 1H); 7.12 (s, 1H); 6.10(d, 1H); 5.52 (d, 1H).

EXAMPLE 31

Cis-[[4-(3,10-dibromo-8-chloro-6,11-dihydro-5H-benzo[5,6]cyclohepta[1,2-b]pyridin-11(R)-yl)-1-piperidinyl]carbonyl]-cyclobutanecarboxamide

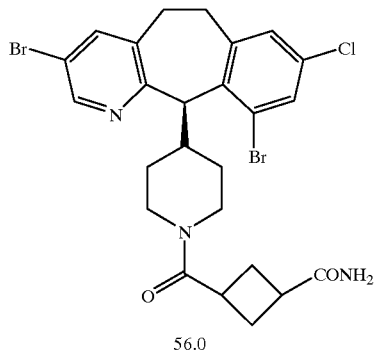
56.0

Step 1: Cis-methyl -[[4-(3,10-dibromo-8-chloro-6,11-dihydro-5H-benzo[5,6]cyclohepta[1,2-b]pyridin-11(R)-yl)-1-piperidinyl]carbonyl] cyclobutanecarboxylate

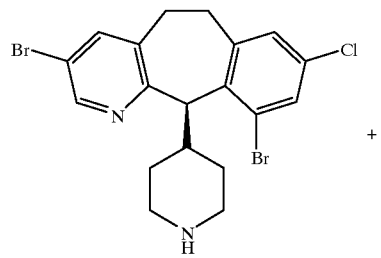

+

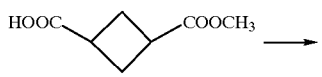

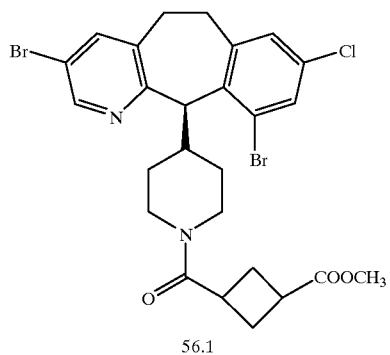
56.1

Use the procedure of example 29, step 1, substituting cis-cyclobutane-1,3-dicarboxylic acid monomethyl ester (prepared as described in Heterocycles 34, 4, 739,1992) to give the title compound(56.1)

Step 2:

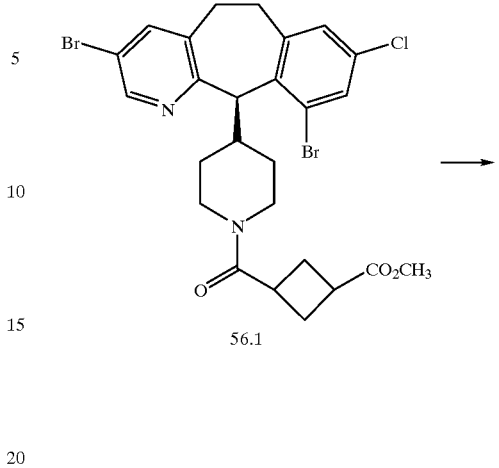
56.1

56.0

Use the procedure described in Example 29, step 2, prepare the title compound (56.0).

EXAMPLE 32

Cis-[[4-(3,10-dibromo-8-chloro-6,11-dihydro-5H-benzo[5,6]cyclohepta[1,2-b]pyridin-11(R)-yl)-1-piperidinyl]-2-oxoethyl]-1-cyclopropanecarboxamide

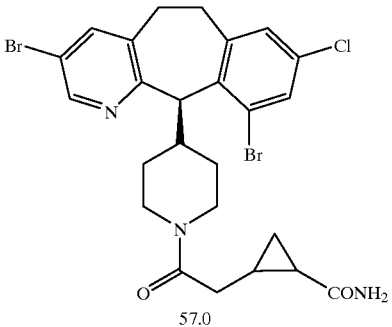
57.0

Step 1: Cis-methyl -[[4-(3,10-dibromo-8-chloro-6,11-dihydro-5H-benzo[5,6]cyclohepta[1,2-b]pyridin-11(R)-yl)-1-piperidinyl]-2-oxoethyl] cyclopropanecarboxylate

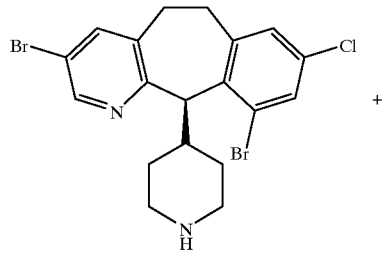

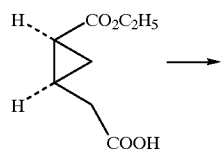

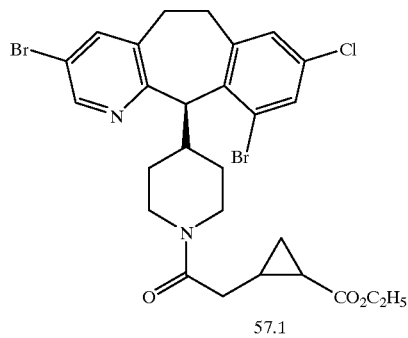

Use the procedure of example 29, step 1, substituting cis-2-carboxymethyl-cyclopropanecarboxylic acid ethyl ester(prepared as described in J.Org.Chem.; 2681,1988) to give the title compound Step 2:

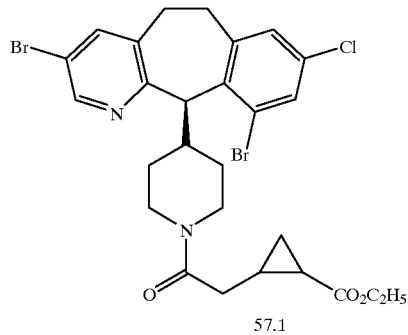

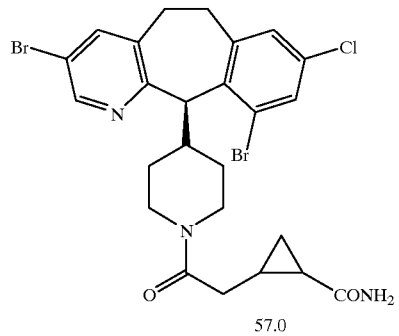

Use the procedure described in Example 29, step 2, prepare the title compound (57.0)

EXAMPLE 33

Trans-[[4-(3,10-dibromo-8-chloro-6,11-dihydro-5H-benzo[5,6]cyclohepta[1,2-b]pyridin-11(R)-yl)-1-piperidinyl]-2-oxoethyl]-1-cyclopropanecarboxamide

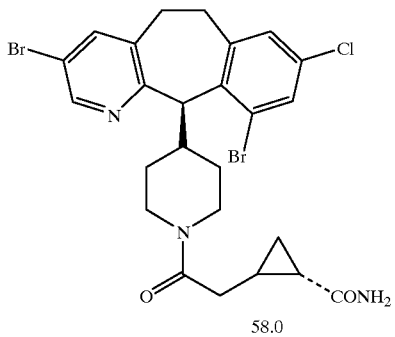

Step 1: Trans-methyl -[[4-(3,10-dibromo-8-chloro-6,11-dihydro-5H-benzo[5,6]cyclohepta[1,2-b]pyridin-11(R)-yl)-1-piperidinyl]-2-oxoethyl] cyclopropanecarboxylate

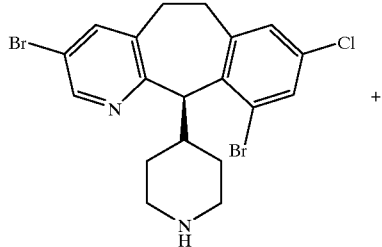

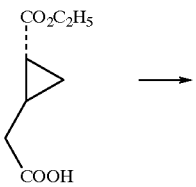

-continued

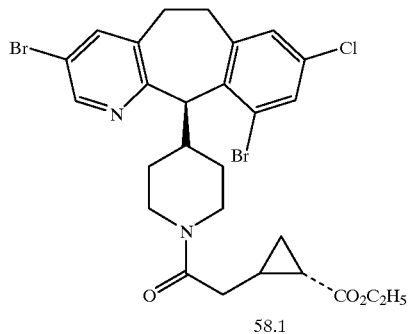
58.1

Use the procedure of Example 29, step 1, substituting cis-2-carboxymethyl-cyclopropanecarboxylic acid ethyl ester(prepared as described in J.Org.Chem.; 2681,1988) to give the title compound (58.1)

Step 2:

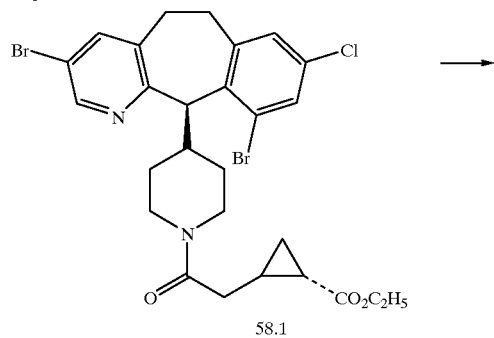

Use the procedure described in Example 29, step 2, prepare the title compound (58.0)

EXAMPLE 34

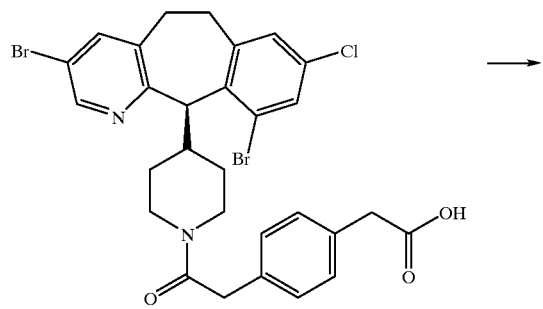

-continued

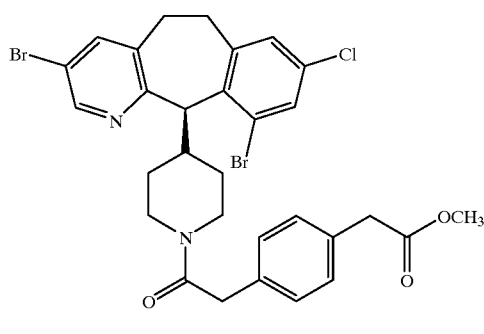

To a solution of compound 28.0 from Example 3 (0.10 g, 0.16 mmol) in MeOH (5 mL) was added catalytic concentrated $H_2SO_4$ (3 drops). The resulting solution was stirred at room temperature 14 hours, diluted with $H_2O$ (10 mL) and EtOAc (15 mL), separated and the organic layer washed with saturated $NaHCO_3$ (10 mL), $H_2O$ (10 mL), dried over $Na_2SO_4$, and concentrated in vacuo. The crude product was purified by flash chromatography (EtOAc) to give compound 59.0 (0.089 g, 88% yield) mp=81–86° C.

EXAMPLE 35

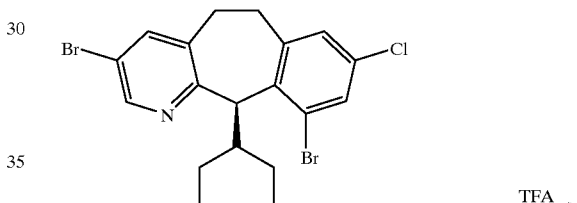

$\xrightarrow{\text{TFA}}{\text{CH}_2\text{Cl}_2}$

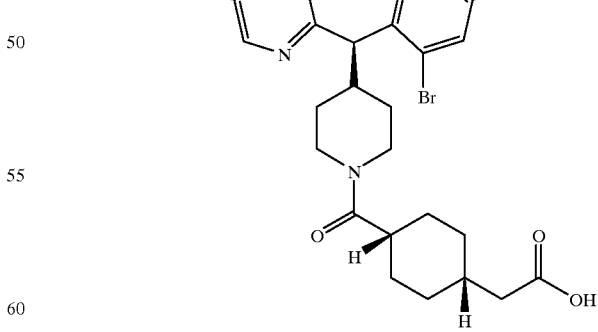

The cis-t-butyl ester, compound 34.0 of Example 9 was hydrolyzed in accordance with the procedure of Preparative Example 11C to give the cis-acid, compound 60.0.

EXAMPLE 36

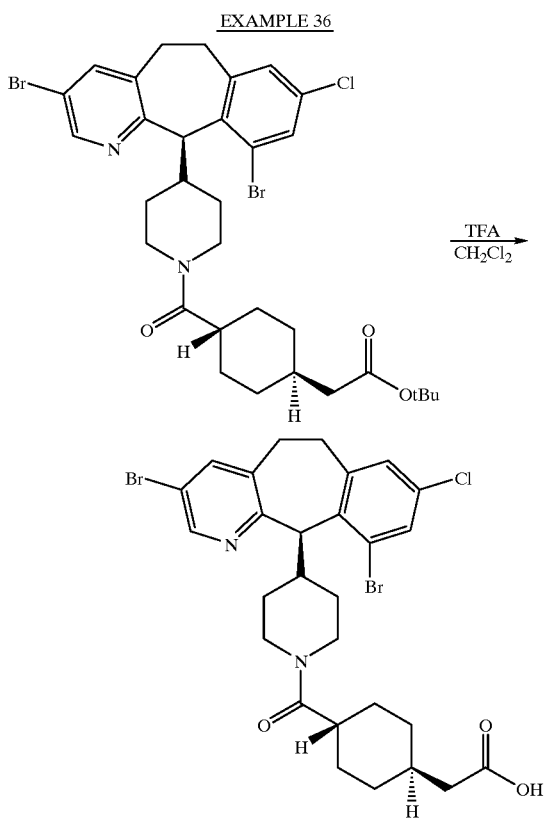

The trans-t-butyl ester, compound 35.0 of Example 10 was hydrolyzed in accordance with the procedure of Preparative Example 11C to give the trans-acid, compound 61.0.

ASSAYS

FPT $IC_{50}$ (inhibition of farnesyl protein transferase, in vitro enzyme assay) and COS Cell $IC_{50}$ (Cell-Based Assay) were determined following the assay procedures described in WO 95/10516, published Apr. 20, 1995. GGPT $IC_{50}$ (inhibition of geranylgeranyl protein transferase, in vitro enzyme assay), Cell Mat Assay, and anti-tumor activity (in vivo anti-tumor studies) could be determined by the assay procedures described in WO 95/10516. The disclosure of WO 95/10516 is incorporated herein by reference thereto.

Additional assays can be carried out by following essentially the same procedure as described above, but with substitution of alternative indicator tumor cell lines in place of the T24-BAG cells.

The assays can be conducted using either DLD-1-BAG human colon carcinoma cells expressing an activated K-ras gene or SW620-BAG human colon carcinoma cells expressing an activated K-ras gene.

Using other tumor cell lines known in the art, the activity of the compounds of this invention against other types of cancer cells could be demonstrated.

Soft Agar Assay:

Anchorage-independent growth is a characteristic of tumorigenic cell lines. Human tumor cells are suspended in growth medium containing 0.3% agarose and an indicated concentration of a farnesyl transferase inhibitor. The solution is overlayed onto growth medium solidified with 0.6% agarose containing the same concentration of farnesyl transferase inhibitor as the top layer. After the top layer is solidified, plates are incubated for 10–16 days at 37° C. under 5% $CO_2$ to allow colony outgrowth. After incubation, the colonies are stained by overlaying the agar with a solution of MTT (3-[4,5-dimethylthiazol-2-yl]-2,5-diphenyltetrazolium bromide, Thiazolyl blue) (1 mg/mL in PBS). Colonies can be counted and the $IC_{50}$'s can be determined.

The results are given in Table 6. In Table 6, "$\mu M$" represents micromolar.

TABLE 6

| Compound of Example | FPT $IC_{50}$ ($\mu M$) | COS Cell $IC_{50}$ ($\mu M$) |
|---|---|---|
| 1 | 0.066 | — |
| 2 | 34% @ 1.0 | — |
| 3 | 0.0016 | 0.38 |
| 4 | 0.0041 | 0.40 |
| 5 | 0.046 | — |
| 6 | 0.019 | — |
| 7 | 0.11 | — |
| 8 | 0.0056 | 0.022 |
| 9 | 0.044 | — |
| 10 | 0.091 | — |
| 11 | 0.25 | — |
| 12 | 0.0019 | 0.010 |
| 13 | 0.0015 | 0.010 |
| 14 | 0.0052 | 0.055 |
| 15 | 0.0036 | 0.10 |
| 16 | 0.0063 | 0.375 |
| 17 | 0.0095 | 0.41 |
| 18 | 0.0053 | 0.45 |
| 19 | 0.0047 | 0.090 |
| 20 | >0.14 | — |
| 21 | 31% @ 14 | — |
| 22 | 0.0063 | 0.022 |
| 23 | 0.0046 | 0.018 |
| 24 | 0.047 | — |
| 25 | 0.036 | — |
| 26 | 0.056 | — |
| 27 | 0.053 | — |
| 28 | 45% @ 1.0 | — |
| 29 (compound 54.1) | 0.34 | — |
| 29 (compound 54.0) | 0.0083 | — |
| 30 (compound 55.1) | 0.025 | — |
| 30 (compound 55.0) | 0.0062 | 0.050 |
| 34 | 0.0086 | 0.18 |
| 35 | 0.0033 | 0.07 |
| 36 | 0.0102 | 0.50 |

The compounds of Examples 8, 12, 13, 14 and 15 had a soft agar $IC_{50}$ of >0.5 $\mu M$.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose.

Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

| Pharmaceutical Dosage Form Examples EXAMPLE A Tablets | | | |
|---|---|---|---|
| No. | Ingredients | mg/tablet | mg/tablet |
| 1. | Active compound | 100 | 500 |
| 2. | Lactose USP | 122 | 113 |

-continued

| Pharmaceutical Dosage Form Examples EXAMPLE A Tablets | | | |
|---|---|---|---|
| No. | Ingredients | mg/tablet | mg/tablet |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

| EXAMPLE B Capsules | | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the formula:

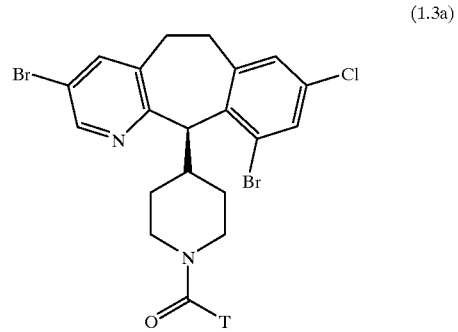

(1.3a)

T represents

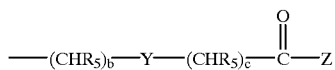

wherein $R_5$ represents H or $(C_1-C_6)$alkyl; b and c are independently 0 to 3; and Y represents

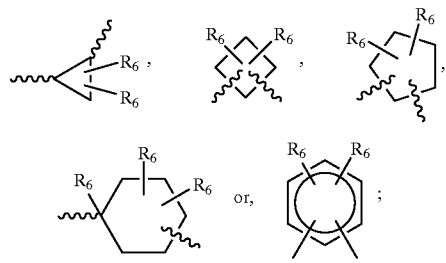

and when T represents

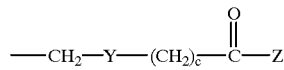

and c is 0 or 1, and Y is cyclopropyl, cyclohexyl or phenyl, then Z, in addition to the definition below, is also NHO$(C_1-C_6)$alkyl or NH$(C_1-C_6)$alkylCO$(C_1-C_6)$alkoxy;

$R_6$ represents $(C_1-C_6)$alkyl or H;

Z represents $OR_7$, $R_7$ or $NR_8R_9$;

$R_7$ represents H, $(C_1-C_6)$alkyl or $(C_1-C_6)$alkyl substituted by $OR_5$, $COR_5$, phenyl or heteroaryl;

$R_8$ and $R_9$ independently represent H, OH, $(C_1-C_6)$alkyl or $(C_1-C_6)$ alkyl substituted by $COR_5$, phenyl, or heteroaryl, or $R_8$ and $R_9$ taken together with the nitrogen atom in $NR_8R_9$ form an unsubstituted or substituted five or six membered heterocyclic ring system containing carbon and one to four heteroatoms selected from N, O, S, SO or $SO_2$, said heterocyclic substituents being $(C_1-C_8)$ alkanoyl, $(C_1-C_6)$alkyl or $(C_1-C_6)$ penthalo alkyl; and provided that when b is 0 then Y is not

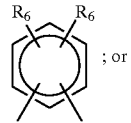; or

T represents

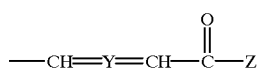

wherein =Y= represents

.

2. The compound of claim 1 wherein T is

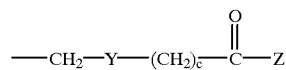

wherein c is 0 or 1, Y is cyclopropyl, cyclohexyl or phenyl and Z is OH, or $OR_5$, $NH_2$, $NR_8R_9$, $NHOR_5$ or $NH(C_1-C_6)$alkylCO$(C_1-C_6)$alkoxy wherein $R_5$, $R_8$ and $R_9$ each represent $(C_1-C_6)$alkyl.

3. The compound of claim 2 wherein c is 0.

4. A compound represented by the formula:

(1.16)

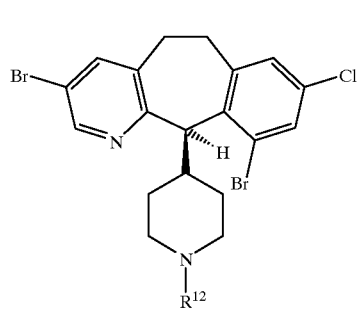

wherein $R^{12}$ is selected from:

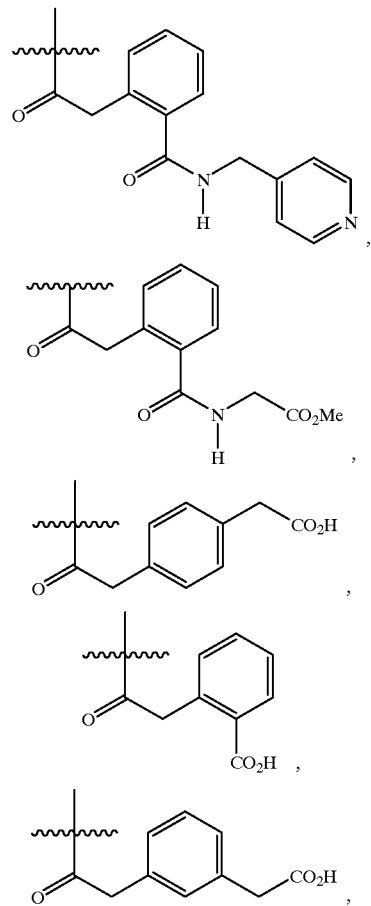

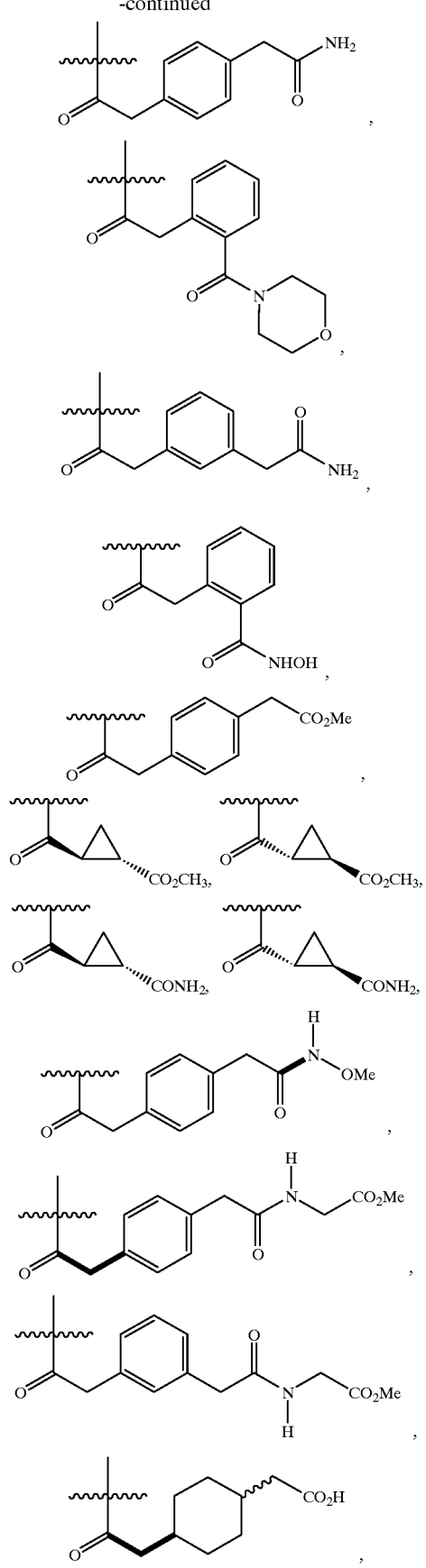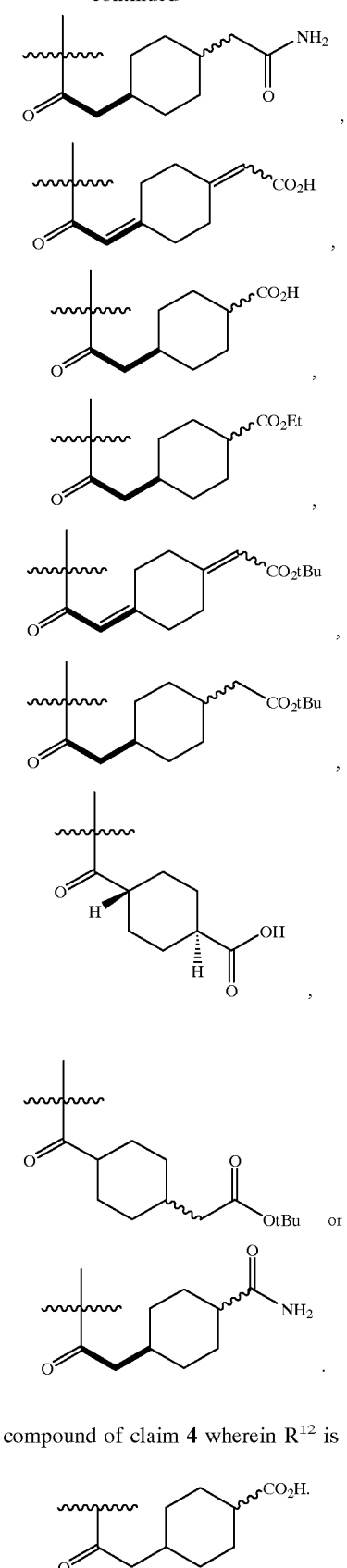
5. The compound of claim 4 wherein $R^{12}$ is

6. A compound of the formula:

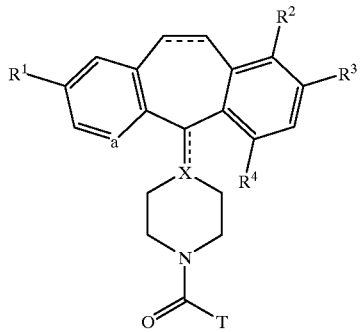
(1.0)

or a pharmaceutically acceptable salt or solvate thereof, wherein:

a represents N;

$R^1$, $R^3$ and $R^4$ are halo and $R^2$ is H; or $R^1$, $R^2$ and $R^3$ are halo and $R^4$ is H;

the dotted line (---) represents an optional bond;

X is C when the optional bond is present, or CH when the optional bond is absent;

T represents

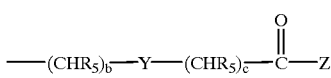

wherein $R_5$ represents H; b and c are independently 0 to 3; and Y represents

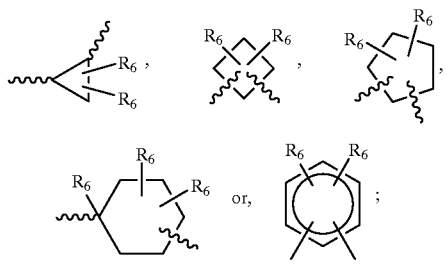

and when T represents

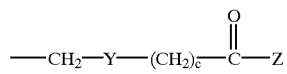

and c is 0 or 1, and Y is cyclopropyl, cyclohexyl or phenyl, then Z in addition to the definition below, is also NHO$(C_1-C_6)$alkyl or NH$(C_1-C_6)$alkylCO$(C_1-C_6)$alkoxy;

$R_6$ represents H;

Z represents $OR_7$ or $NR_8R_9$;

$R_7$ represents H or $(C_1-C_6)$alkyl;

$R_8$ and $R_9$ independently represent H, OH or $(C_1-C_6)$ alkyl substituted by $COR_5$ (wherein $R_5$ represents H or a $(C_1-C_6)$alkyl) or heteroaryl, or $R_8$ and $R_9$ taken together with the nitrogen atom in $NR_8R_9$ form

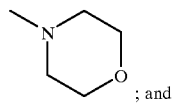; and provided that when b is 0 then Y is not

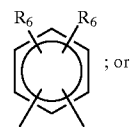; or

T represents

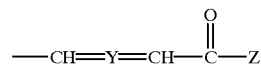

wherein =Y= represents

7. A method of treating tumor cells wherein the tumor cells treated are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, breast tumor cells and prostate tumor cells in a human by inhibition of farnesyl protein transferase comprising administering to a human in need thereof a compound of claim 6 in an amount that inhibits farnesyl protein transferase.

8. A method of inhibiting farnesyl protein transferase in a human comprising the administration of the compound of claim 6 to a human in need thereof in an amount that inhibits farnesyl protein transferase.

9. A pharmaceutical composition comprising an effective amount of a compound of claim 6 in combination with a pharmaceutically acceptable carrier.

10. The compound of claim 6 wherein $R^1$ is Br, $R^3$ is Cl and $R^4$ is Br.

11. The compound of claim 10 wherein X is CH.

12. A compound of the formula:

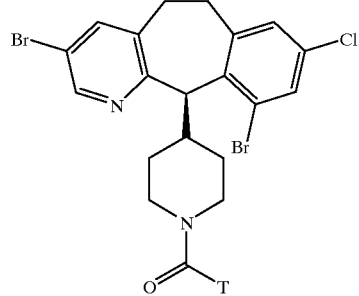
(1.9)

or a pharmaceutically acceptable salt or solvate thereof, wherein:

T represents

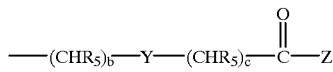

wherein $R_5$ represents H; b and c are independently 0 to 3; and Y represents

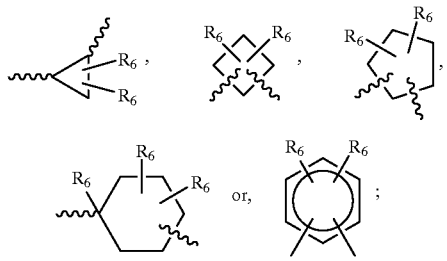

and when T represents

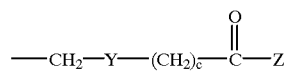

and c is 0 or 1, and Y is cyclopropyl, cyclohexyl or phenyl, then Z, in addition to the definition below, is also NHO($C_1$–$C_6$)alkyl or NH($C_1$–$C_6$)alkylCO($C_1$–$C_6$alkoxy;

$R_6$ represents H;

Z represents $OR_7$ or $NR_8R_9$;

$R_7$ represents H or ($C_1$–$C_6$)alkyl;

$R_8$ and $R_9$ independently represent H, OH or ($C_1$–$C_6$) alkyl substituted by $COR_5$ (wherein $R_5$ represents H or a ($C_1$–$C_6$)alkyl) or heteroaryl, or $R_8$ and $R_9$ taken together with the nitrogen atom in $NR_8R_9$ form

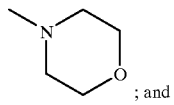 ; and provided that when b is 0 then Y is not

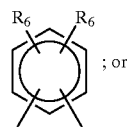 ; or

T represents

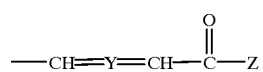

wherein =Y= represents

.

13. A method of treating tumor cells wherein the tumor cells treated are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, breast tumor cells and prostate tumor cells in a human by inhibition of farnesyl protein transferase comprising administering to a human in need thereof a compound of claim 4 in an amount that inhibits farnesyl protein transferase.

14. A method of inhibiting farnesyl protein transferase in a human comprising the administration of the compound of claim 4 to a human in need thereof in an amount that inhibits farnesyl protein transferase.

15. A pharmaceutical composition comprising an effective amount of a compound of claim 4 in combination with a pharmaceutically acceptable carrier.

16. A method of treating tumor cells wherein the tumor cells treated are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, breast tumor cells and prostate tumor cells in a human by inhibition of farnesyl protein transferase comprising administering to a human in need thereof a compound of claim 12 in an amount that inhibits farnesyl protein transferase.

17. A method of inhibiting farnesyl protein transferase in a human comprising the administration of the compound of claim 12 to a human in need thereof in an amount that inhibits farnesyl protein transferase.

18. A pharmaceutical composition comprising an effective amount of a compound of claim 12 in combination with a pharmaceutically acceptable carrier.

19. The compound of claim 6 wherein T represents

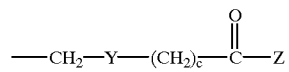

wherein c is 0 or 1;

Y is cyclopropyl, cyclohexyl or phenyl; and

Z is OH, $OR_5$, $NH_2$, $NR_8R_9$, NHO($C_1$–$C_6$)alkyl or NH($C_1$–$C_6$)alkylCO($C_1$–$C_6$)alkoxy wherein $R_5$, $R_8$ and $R_9$ each represent ($C_1$–$C_6$)alkyl.

20. The compound of claim 12 wherein T represents

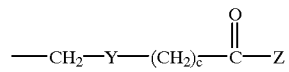

wherein c is 0 or 1;

Y is cyclopropyl, cyclohexyl or phenyl; and

Z is OH, $OR_5$, $NH_2$, $NR_8R_9$, NHO($C_1$–$C_6$)alkyl or NH($C_1$–$C_6$)alkylCO($C_1$–$C_6$)alkoxy wherein $R_5$, $R_8$ and $R_9$ each represent ($C_1$–$C_6$)alkyl.

21. The compound of claim 12 selected from:

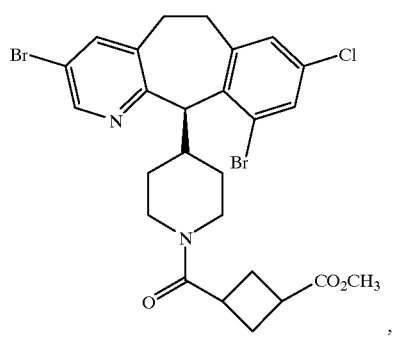

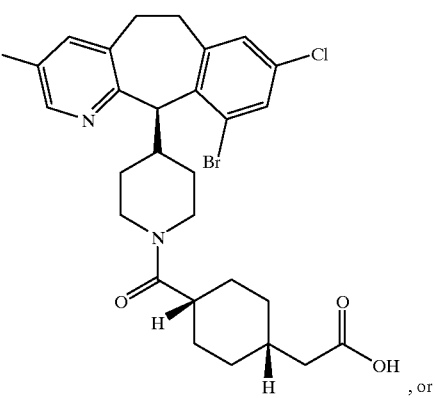
, or

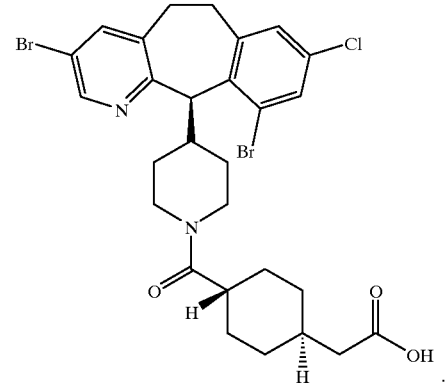
.

22. A method of treating tumor cells wherein the tumor cells treated are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, breast tumor cells and prostate tumor cells in a human by inhibition of farnesyl protein transferase comprising administering to a human in need thereof a compound of claim 21 in an amount that inhibits farnesyl protein transferase.

23. A method of inhibiting farnesyl protein transferase in a human comprising the administration of the compound of claim 21 to a human in need thereof in an amount that inhibits farnesyl protein transferase.

24. A pharmaceutical composition comprising an effective amount of a compound of claim 21 in combination with a pharmaceutically acceptable carrier.

* * * * *